(12) United States Patent
Boireau et al.

(10) Patent No.: US 7,993,860 B2
(45) Date of Patent: Aug. 9, 2011

(54) **POLYPEPTIDES RECOGNIZED BY ANTI-*TRICHINELLA* ANTIBODIES, AND USES THEREOF**

(75) Inventors: Pascal Boireau, Bondoufle (FR); Mingyuan Liu, Changchun (CN); Baoquan Fu, Lanzhou (CN); Danielle Le Rhun, Sucy En Brie (FR); Céline Bahuon, Maisons-Alfort (FR); Isabelle Vallee, Saint Maur des Fosses (FR); Franck Le Guerhier, Brunoy (FR); Romel Hernandez Bello, Mexico (MX); Xiuping Wu, Changchun (CN)

(73) Assignees: Institut National de la Recherche Agronomique, Paris (FR); Agence Francaise de Securite Sanitaire des Aliments, Maisons-Alfort (FR); Jillin University, Changchun (CN)

( * ) Notice: Subject to any disclaimer, the term of this patent is extended or adjusted under 35 U.S.C. 154(b) by 0 days.

(21) Appl. No.: 12/278,595

(22) PCT Filed: Feb. 7, 2007

(86) PCT No.: PCT/FR2007/000221
§ 371 (c)(1),
(2), (4) Date: Feb. 23, 2009

(87) PCT Pub. No.: WO2007/090960
PCT Pub. Date: Aug. 16, 2007

(65) Prior Publication Data
US 2010/0098717 A1    Apr. 22, 2010

(30) Foreign Application Priority Data

Feb. 7, 2006  (FR) ..................... 06 01058

(51) Int. Cl.
*G01N 33/53* (2006.01)
(52) U.S. Cl. ............. 435/7.22; 435/4; 435/7.1; 435/7.2; 424/265.1
(58) Field of Classification Search .................. None
See application file for complete search history.

(56) References Cited

U.S. PATENT DOCUMENTS
5,422,263 A   6/1995 Zarlenga, Jr. et al.

FOREIGN PATENT DOCUMENTS
WO    WO2007/090960    8/2007

OTHER PUBLICATIONS

Polvere R.I., et al ("*Trichinella spiralis* clone 17.20.". Submitted (Feb. 1997) to the EMBL/GenBank/DDBJ databases.*
Swissprot No. Q6RUJ3 "Newborn larvae-specific serine protease SS2-1." (Dec. 2003).
Swissprot No. Q9BJL7 "Newborn larvae-specific serine protease SS2." (Dec. 2000).
Nagano, et al. (2003) "Molecular Cloning and Characterization of a Serine Proteinase Gene of *Trichinella spiralis*." J. Parasitol. 89(1): 92-98.
Nagano, et al. (2001) "Molecular Cloning and Characterization of a 21 kDa Protein Secreted from *Trichinella pseudospiralis*." Journal of Helminthology 75: 273-278.
Lun, et al. (2003) "Characterization and Cloning of Metallo-Proteinase in the Excretory/Secretory Products of the infective-stage larva of *Trichinella spiralis*." Parasitol Res 90: 27-37.
Romaris, et al. (2002) "A Putative Serine Protase Among the Excretory-Secretory Glycoproteins of L1 *Trichinella spiralis*." Molecular & Biochemical Parasitology 122: 149-160.
Boireau, et al. (2004) "*Trichinella* Antigens and Immunodominant Epitopes." IX European Multicolloquium of Parasitology 181-188.
Dea-Ayuela et al., Veterinary Research, vol. 30, pp. 559-571 (1999).
Moczon et al., Parasitology Research, vol. 85, pp. 47-58 (1999).
Perteguer et al., Molecular Immunology, vol. 41, pp. 421-433 (2004).
Romaris et al., Parasite Immunology, vol. 25, pp. 297-305 (2003).
Todorova et al., Parasitology Research, vol. 86, pp. 684-687 (2000).
Trap et al., Xth international Conference on *Trichinellosis*-Fontainebleau, France, p. 39, Aug. 20-24, 2000.

* cited by examiner

*Primary Examiner* — Jennifer Graser
(74) *Attorney, Agent, or Firm* — Hunton & Williams LLP

(57) ABSTRACT

The present invention relates to new polypeptides recognized by anti-*Trichinella* antibodies. The invention also relates to the use of said polypeptides for the detection of anti-*Trichinella* antibodies and for the prevention of trichinellosis.

36 Claims, 5 Drawing Sheets

MGSDKIIHLTDDSFDTDVLKADGAILVDFWAHWCGPCKMIAPILDEIADEYQGKLTVAKLNI
DHNPGTAPKYGIRGIPTLLLFKNGEVAATKVGALSKGQLKEFLDANLAGSGSGDDDDKLGID
PFTENSPEGTVKWASKEDSPVDLSTASRPTNPYTGSRPTSPSSGSRPTYPSSGSRPTSPS
SGSRPTYPSSGSRPTYPSSGSRPTYPYTGSRPTPQKPVFPSYQKYPPAVQKYIDSLPSGTQG
TLEYTVTQNGVTTTTKGELKLEGKPIPNPLLGLDSTRTGHHHHHH

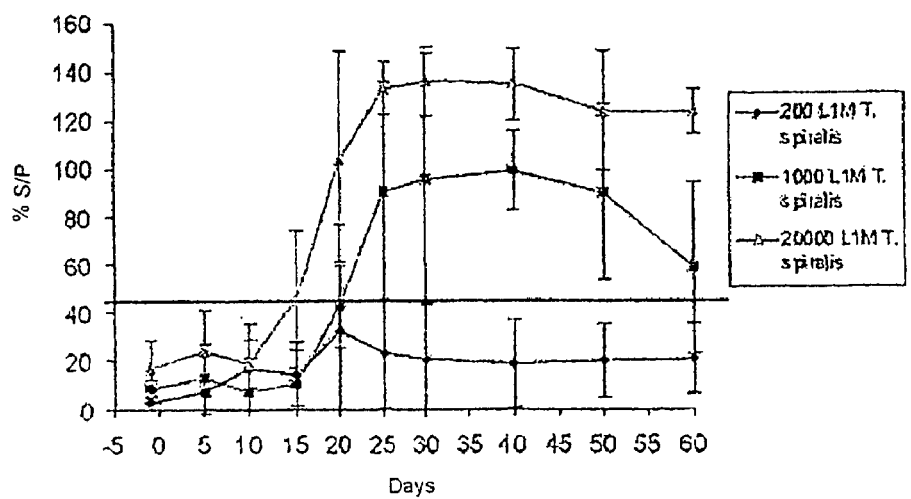
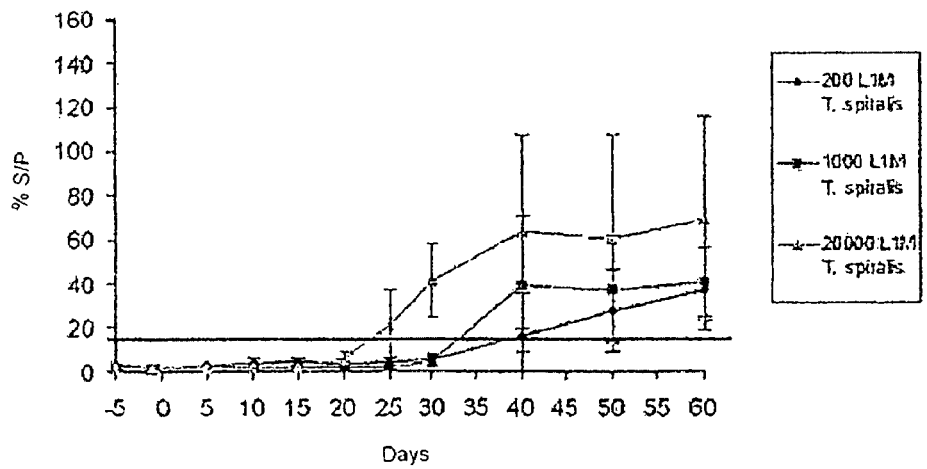
Figure 3

MGSDKIIHLTDDSFDTDVLKADGAILVDFWAHWCGPCKMIAPILDEIADEYQGKLTVAKLNI
DHNPGTAPKYGIRGIPTLLLFKNGEVAATKVGALSKGQLKEFLDANLAGSGSGDDDDKLGID
PFTRENMHCQFILSLLLFSLNVVFFEAAKSLDAVDDELKRCTEKQTEICAQTECKAEDAIMT
DLLLEGESDITDHPDFLLYATCMQRCCARLNGAQVAPLKEEEKRRGPSKLPFQSIFEVADQK
TVERCDETMCKSYRKKYENLVALTSSYKKLRSSQELKDYKQCIERCDAKLNGKGELKLEGKP
IPNPLLGLDSTRTGHHHHHH

Figure 5

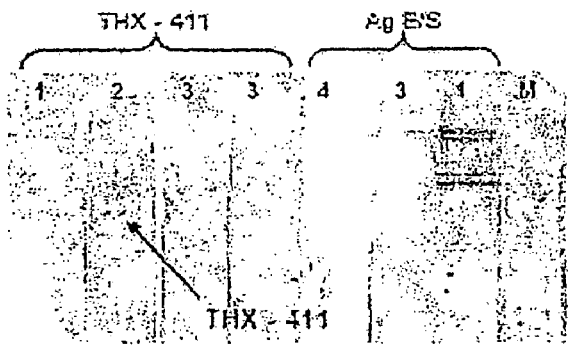

Figure 6

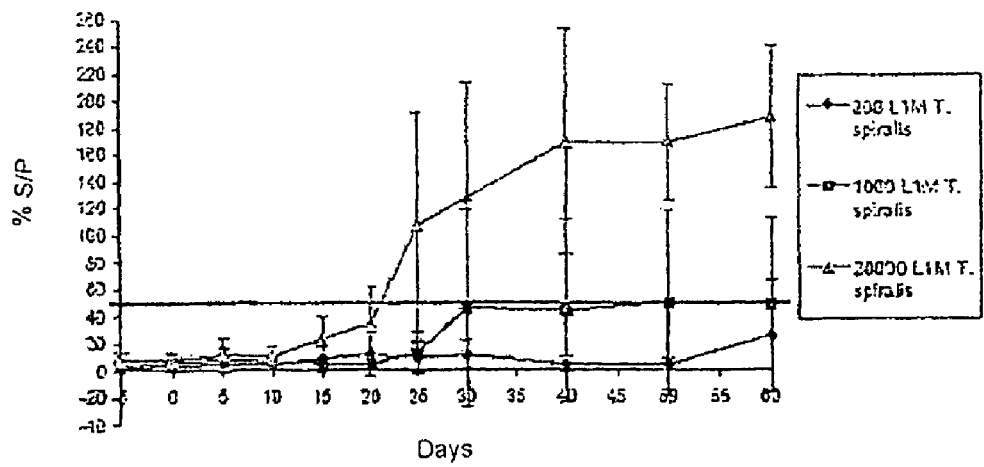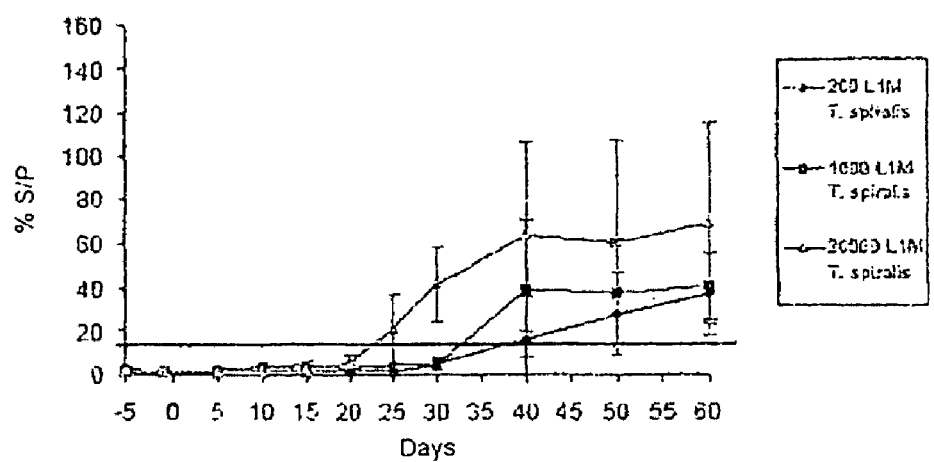
Figure 7 ced by the pigs (DUPOUY-CA-
POLYPEPTIDES RECOGNIZED BY ANTI-*TRICHINELLA* ANTIBODIES, AND USES THEREOF

CROSS-REFERENCE TO RELATED APPLICATIONS

This application is the national stage application of International Patent Application No. PCT/FR2007/000221, filed Feb. 7, 2007, which claims the benefit of French Patent Application No. FR 06/01058, filed Feb. 7, 2006, the disclosures of each of which are hereby incorporated by reference.

BACKGROUND OF THE INVENTION (i) Field of the Invention

The present invention relates to the use of new antigens identified in the parasite *Trichinella* in the context of the diagnosis and the prevention of trichinellosis.

(ii) Description of the Related Art

Trichinellosis is a zoonosis associated with the consumption of meat infested with the parasite *Trichinella* (MURRELL et al., 2000).

This nematode of the class Adenophorea belongs to the family Trichinellidae which comprises 8 species and 3 genotypes that are related, in 2 phylogenetically distinct groups: on the one hand, the encapsulated trichinae (*T. spiralis; T. nativa; T. britovi; T. murrelli; T. nelsoni*) which infest mammals, end on the other hand, the nonencapsulated trichinae (*T. pseudospiralis; T. papuae; T. zimbabwensis*) which infest mammals, birds and reptiles (GASSER et al., 2004). All these species can infest humans.

The biological cycle of the parasite is autoheteroxenous: it takes place entirely in the same host, which is successively the definitive host (carrying adult parasites) and the intermediate host (carrying infesting larvae) (BOIREAU et al., 2002). The passing of the infesting larvae from host to another is necessary in order for a new cycle to be carried out. This passage occurs through the ingestion of raw or barely cooked meat contaminated with the larvae. During digestion, the latter are released, and penetrate the intestinal epithelium, where they will mature into sexual adult (Ad) worms. The fertilized females subsequently expel newborn L1 larvae (L1NN) which reach the striated muscles via the lymphatic circulation and the blood stream. These L1NN larvae penetrate the muscle cells (infesting development stage L1M: L1 muscle larva), of which they bring about the dedifferentiation into feeder cells surrounded by a protective collagen capsule which is thick in the case of encapsulated trichinae, very thin in the case of "nonencapsulated" trichinae.

Although trichinellosis is asymptomatic in animals, human infestation is reflected, during the initial intestinal phase, by diarrhea associated with nausea, vomiting and violent abdominal pain, while the symptoms associated with the muscle invasion phase are characterized by the combination of fever, facial edema and myalgia (CAPO & DESPOMMIER, 1996). Ocular, pulmonary, gastrointestinal, cardiac and neurological attacks can also add to this clinical picture of trichinellosis, the progression of which can be lethal. The chronic nature of the infestation, marked by persistent muscle pain in patients, is associated with the survival of the parasite in the feeder cell.

The specific treatment of human trichinellosis with anthelminthics is all the more effective if the diagnosis of the infestation is made early so as to allow action against all the parasitic stages and especially before the formation of the protective collagen capsule around the L1M larvae (FOURESTIE et al., 1988).

The epidemiological data have demonstrated a geographical distribution of the parasite in all parts of the world, associated with a method of transmission involving many species of the wild-type fauna which also maintain a domestic infestation cycle mainly represented by the pigs (DUPOUY-CAMET, 2000).

Epidemics of human trichinellosis, an emerging or reemerging zoonosis, constitute a real public health problem throughout the world owing to dietary habits and hygiene controls that are not always effective (MURRELL & POZIO, 2000). These epidemics essentially involve pig and wild boar meat and also horse meat (BOIREAU et al., 2000).

The prevention of human contamination therefore involves cooking meat right through and improving rearing conditions and/or conditions for controlling animal trichinellosis (pigs, horses, wild boar and other wild animal species sensitive to *Trichinella*) (BOIREAU et al., 2002).

The screening techniques for trichinellosis can be divided into two categories: 1) direct detection of the L1M larvae, by trichinoscopy (microscopic observation of a meat fragment), or after artificial digestion of muscle samples, and 2) indirect detection by various immunological methods, for detecting antibodies directed against the *Trichinella* antigens.

Each of the developmental stages of the parasite: adult (Ad), newborn larva (L1NN) and muscle larva (L1M) has a corresponding specific antigen profile.

It is antigen preparations derived from L1M-stage larvae which are currently used for immunodiagnosis. This is because the antigen fractions of the two early stages Ad and L1NN are difficult to purify, and it had not been possible to identify immunodominant antigens associated with one and/or the other of these two stages up until now.

Either preparations of total soluble antigen, obtained by lysis of the larvae, centrifugation of the lysate and recovery of the supernatant, or, more commonly, excretion/secretion antigens (E/S antigens) are principally used.

The excretion-secretion antigens are produced when L1M larvae are placed under survival conditions in a culture medium; they originate from a particular organ, called the stichosome, which comprises about fifty discoid cells, the stichocytes. The stichocytes contain granules, the content of which is evacuated by a canaliculus into the lumen of the parasite's esophagus. This content, which is very highly antigenic, constitutes a part of the excretion-secretion antigens. These antigens form a complex mixture of proteins, containing in particular a group of glycoproteins (called TSL1 antigens) bearing a specific carbohydrate molecule, known only in *Trichinella* and present in all the species of this parasite, beta-tyvelose.

The preparations of excretion-secretion antigens which are currently used as a reference in terms of immunodiagnosis of trichinellosis are obtained from culture medium of *Trichinella spiralis* L1M larvae. After culture for 18 to 20 hours, the medium is recovered by filtration and then concentrated (GAMBLE et al., 1983; GAMBLE et al., 1988).

The principal drawback of the preparations of total soluble antigen is their lack of specificity. Antigen cross reactions with other parasitoses are commonly observed. The excretion-secretion antigens make it possible to obtain a better specificity. However, in both cases, it is difficult to produce standardized batches of antigen in large amounts.

The saccharide structure containing beta-tyvelose, which represents an immunodominant epitope of E/S antigen preparations (REASON et al., 1994; U.S. Pat. Nos. 5,541,075 and 5,707,817), has been synthesized chemically, and its use for the immunodiagnosis of *Trichinella* has been proposed.

This reagent has good specificity, but its sensitivity appears to be lower than that of E/S antigen preparations. In addition, the chemical synthesis of this structure remains expensive and laborious to carry out.

Another problem encountered in the context of the serological diagnosis of *Trichinella* is the existence of a "blind window" of detection corresponding to the early stages of infestation, which is reflected by false-negative results. In addition, in horses, gradual disappearance of the antibodies has been observed 25 weeks after infestation.

The inventors have undertaken to identify immunodominant antigens associated with the early stages of *Trichinella* infestation and which can be used for the serological diagnosis of trichinellosis, in order to provide means for obtaining early, specific and sensitive detection of *Trichinella* infestations, both in humans and in animals. With this aim, they have investigated whether there existed, among the products of the genes expressed by *Trichinella* at the L1NN stage and/or at the Ad stage, proteins which would possess the desired antigenic properties.

In this context, they have discovered that a *Trichinella spiralis* protein which is part of the proteins expressed specifically at the L1NN stage in this organism, constitutes an immunodominant antigen, allowing early detection of the humoral response directed against *Trichinella*, and that it is also conserved between various species of *Trichinella*.

This protein will hereinafter be referred to as NBL1. The complete cDNA sequence encoding this protein and also the polypeptide sequence which is deduced therefrom are respectively accessible on Genbank under numbers AF331160 and AAK16520 (also known as Swissprot Q9BJL7); these sequences are annotated as "serine protease SS2, specific for newborn larvae". These sequences are also respectively reproduced in the attached sequence listing under numbers SEQ ID NO: 1 and SEQ ID NO: 2. A partial cDNA sequence encoding this protein and also the polypeptide sequence which is deduced therefrom are respectively accessible on Genbank under numbers AY491941 and AAR36900 (also known as Swissprot Q6RUJ3).

The inventors have also shown that the immunoreactivity associated with the humoral response directed against NBL1 is located in the C-terminal part of this protein, and have identified an immunodominant epitope responsible for this reactivity.

Furthermore, the inventors have identified, using a cDNA library of mixed early Ad+L1NN stages of *T. spiralis*, a new gene, hereinafter referred to as 411.

The sequence of this gene is represented in the attached sequence listing under the number SEQ ID NO: 3, and that of its translation product under the number SEQ ID NO: 4. This product of translation of this gene is related (78.7% identity) to an E/S antigen, known as Tp21-3 protein, identified in *T. pseudospiralis* (AAF79206; NAGANO et al., 2001), and also to the product of translation of the hypothetical ORF 17.20 of *T. spiralis* (AAB48489), with which it exhibits 86.6% identity.

The 411 gene translation product also makes it possible to detect, at an early stage, the humoral response directed against various species of *Trichinella*.

In addition, each of the NBL1 and 411 antigens has made it possible, in the assays carried out, to detect animals infested with *Trichinella* which were not detected with the other antigen, nor with the E/S antigen, at least during the period D15-D30 post-infestation (pi).

The combination of the NBL1 antigen (or of an immunodominant epitope thereof) with the 411 antigen therefore makes it possible to improve the sensitivity of the diagnosis, in particular at the early stages of infestation (15 to 20 days after infestation).

Consequently, a subject of the present invention is the use of an antigenic polypeptide recognized by anti-*Trichinella* antibodies as a reagent for detecting anti-*Trichinella* antibodies in a biological sample, characterized in that said polypeptide is chosen from:

a) a polypeptide comprising an immunodominant epitope of the NBL1 antigen, which epitope is defined by the sequence PSSGSRPTYP (SEQ ID NO: 5);

b) a polypeptide, also referred to hereinafter as 411 antigen, comprising amino acids 25-175 of the sequence SEQ ID NO: 4 (which represent the mature form of the 411 protein), or comprising a sequence having at least 80%, and by order of increasing preference, at least 85%, 90% or 95% identity with the sequence of amino acids 25-175 of the sequence SEQ ID NO: 4.

A subject of the present invention is more particularly a method for detecting the presence of anti-*Trichinella* antibodies in a biological sample, which method is characterized in that it comprises:

bringing said biological sample into contact with one or more polypeptide(s) a) and/or one or more polypeptide(s) b), as defined above, under conditions which allow the formation of an antigen/antibody complex with the anti-*Trichinella* antibodies possibly present in said sample;

detecting, by any appropriate means, the antigen/antibody complex possibly formed.

Generally, said biological sample is a serum sample. It can be obtained from any individual (mammals, bird or reptile) belonging to a species that can be infested with *Trichinella*, and in which it is desired to detect the presence of this parasite. Advantageously, it is a sample obtained from a mammal, for example from a farm animal, or from a human patient.

Advantageously, a mixture comprising one or more polypeptide(s) a) and/or one or more polypeptide(s) b) as defined above is used.

This combination makes it possible in particular to broaden the spectrum of reactivity, relative to each of the polypeptides used individually.

The polypeptides a) defined above, with the exclusion of the whole NBL1 antigen identified by Genbank accession number AAK16520, and of its fragment identified by Genbank accession number AAR36900, are also part, as such, of the subject of the present invention.

Among these polypeptides in accordance with the invention, mention will in particular be made of the polypeptides containing one or more of the following sequences: the sequence: PSSGSRPTYPSSGSR (SEQ ID NO: 6); the sequence PSSGSRPTYPYTGSR (SEQ ID NO: 7); the sequence RPTSPSSGSRPTYPS (SEQ ID NO: 8).

This encompasses, for example, fragments of the C-terminal region of the NBL1 antigen: mention will in particular be made of the fragments containing the following sequence:

```
                                                  (SEQ ID NO: 11)
ENSPEGTVKWASKEDSPVDLSTASRPTNPYTGSRPTSPSSGSRPTYPSSG

SRPTSPSSGSRPTYPSSGSRPTYPSSGSRPTYPYTGSRPTPQKPVFPSYQ

KYPPAVQKYIDSLPSGTQGTLEYTVTQNGVTTTT,
``` which corresponds to amino acids 326-459 of the sequence SEQ ID NO: 2; and subfragments of this sequence SEQ ID NO: 11, in particular those comprising the following sequence:

```
                                       (SEQ ID NO: 9)
PSSGSRPTYPSSGSRPTSPSSGSRPTYPSSGSRPTYPSSGSRPTYP,
``` which corresponds to amino acids 363-409 of the sequence SEQ ID NO: 2, and more particularly, those comprising the following sequence:

```
                                       (SEQ ID NO: 10)
SRPTNPYTGSRPTSPSSGSRPTYPSSGSRPTSPSSGSRPTYPSSGSRPTY
PSSGSRPTYPYTGSRPT,
``` which corresponds to amino acids 349-415 of the sequence SEQ ID NO: 2.

The polypeptides b) defined above, with the exception of those identified by GenBank accession numbers AAF79206 and AAB48489, are part, as such, of the subject of the present invention. Preferred polypeptides are in particular the polypeptide of sequence SEQ ID NO: 4, or the polypeptide corresponding to amino acids 25-175 of the sequence SEQ ID NO: 4, and also the polypeptides having at least 90%, or preferably at least 95%, identity with the sequence SEQ ID NO: 4, or with the sequence of amino acids 25-175 of the sequence SEQ ID NO: 4.

The present invention encompasses in particular chimeric polypeptides comprising one or more copies of the sequence PSSGSRPTYP (SEQ ID NO: 5), or of a fragment of the NBL1 antigen containing this sequence, and/or one or more copies of a polypeptide b) as defined above, optionally fused to one or more other heterologous sequence(s).

A subject of the present invention is also the polynucleotides encoding the polypeptides in accordance with the invention, and also recombinant vectors comprising said polynucleotides, and host cells transformed with said vectors.

A subject of the present invention is also a composition comprising one or more polypeptide(s) a) and one or more polypeptide(s) b), as defined above, and also a composition comprising one or more polynucleotide(s) encoding said polypeptide(s).

The polypeptides a) and b) defined above can be used in the context of various methods for detecting antibodies, which are known in themselves. By way of examples, mention will in particular be made of ELISA type methods (direct, indirect or sandwich), methods of microagglutination on beads, and also methods of electrophoretic blotting coupled to immunolabeling.

A subject of the present invention is also a kit for detecting the presence of anti-*Trichinella* antibodies in a biological sample, characterized in that it comprises one or more polypeptide(s) a) and/or one or more polypeptide(s) b) as defined above, and, where appropriate, buffers and reagents suitable for constituting a reaction medium which allows the formation of an antigen/antibody complex, and, optionally, means for detecting said antigen/antibody complex.

Advantageously, said kit comprises a polypeptide a) and/or a polypeptide b) as defined above, immobilized on a solid support. By way of nonlimiting examples of solid supports that can be used, mention will be made of microtitration plates, beads, microbeads or microparticles, strips, etc.

Said kit may also comprise reference samples, such as one or more negative serum or sera and one or more positive serum or sera.

A subject of the present invention is also the use of a polypeptide a) or of a polypeptide b), as defined above, for preparing antibodies specifically directed against said polypeptide.

These polypeptides may be used in the context of various methods, known in themselves, for preparing antibodies. They may, for example (optionally after the addition of a suitable adjuvant), be used for the immunization of an animal. They may also be grafted onto an affinity chromatography support, in order to make it possible to purify the antibodies specifically directed against the polypeptide concerned, from a biological fluid. The biological fluid may, for example, be the serum of an animal immunized beforehand with the polypeptide concerned, or a hybridoma supernatant; it may also be the serum of an animal infested with *Trichinella*, from which it is desired to isolate a subpopulation of antibodies specifically directed against the polypeptide concerned.

The present invention also encompasses any antibodies specifically directed against a polypeptide a) or a polypeptide b) as defined above. They may be polyclonal or monoclonal antibodies. Preferred antibodies are those recognizing the PSSGSRPTYP epitope (SEQ ID NO: 5).

Antibodies specifically directed against a polypeptide can be obtained by various techniques known in themselves, and in particular by conventional methods comprising the immunization of an animal with the polypeptide concerned (with a suitable adjuvant optionally added thereto), and the recovery of its serum (for the production of polyclonal antibodies), or of its lymphocyte cells (for the production of monoclonal antibodies).

The polypeptides a) and b) defined above, and also the polynucleotides encoding these polypeptides, can be used for the preparation of immunogenic compositions, and in particular of anti-*Trichinella* vaccines.

A subject of the present invention is also an immunogenic composition comprising one or more polypeptide(s) a) and/or one or more polypeptide(s) b) as defined above, or one or more polynucleotide(s) encoding said polypeptide(s), combined with one or more adjuvant(s) for enhancing the immune response.

According to a preferred embodiment of an immunogenic composition in accordance with the invention, it is a vaccine.

A large variety of adjuvants for increasing the immunogenicity of peptides are known in themselves to those skilled in the art: by way of examples of adjuvants, mention will be made of alum (aluminum hydroxide), complete Freund's adjuvant or incomplete Freund's adjuvant (IFA), liposomes, and also virosomes (reconstituted viral envelopes), peptide derivatives of muramic acid, etc. In the case of a vaccine, a pharmacologically acceptable adjuvant will of course be chosen; by way of examples of preferred adjuvants, mention will be made of adjuvants of "water-in-oil" emulsion type, for example the adjuvants sold by the company SEPPIC under the names MONTANIDE ISA 70 and MONTANIDE ISA 775, and which are also described in patents EP 480 982, EP 825 875, U.S. Pat. No. 5,422,109, U.S. Pat. No. 6,251,407 and U.S. Pat. No. 6,610,309.

Where appropriate, in particular in the case of short peptides ($\leq$30 amino acids), said polypeptide(s) may be coupled to a carrier protein.

By way of examples of carrier proteins, mention will in particular be made of KLH (keyhole limpet hemocyanin), bovine serum albumin (BSA), ovalbumin, tetanus toxoid or diphtheria toxoid. It is also possible to form a multiepitope composition, by associating several copies of the same peptide with one another, and optionally with other peptide epitopes, in the form of chimeric polypeptides, or by means of a polymeric chain, for example a polylysine.

If a polynucleotide is used as immunogen, the immunogenic composition may be in the form of a recombinant vector into which the polynucleotide(s) to be administered is (are) inserted. Use may, for example, be made of viral vectors such as poxviruses, andenoviruses, retroviruses, lentiviruses, herpesviruses and AAVs (adeno-associated viruses), etc. It may also be in the form of a nonpathogenic bacterium, transformed with one or more expression vectors containing said polynucleotide(s). The polynucleotide(s) may also be administered directly, in the form of naked DNA, or it (they) may be incorporated into liposomes. In the case of a vaccine, use will preferably be made of a nonpathogenic bacterium (for example a lactobacillus, or a nonpathogenic strain of *Escherichia coli* or of *Salmonella suis*), or a vector derived from a vaccinal viral strain; for example, a vector derived from a vaccinal strain of the pseudorabies (Aujeszky's disease) virus.

The present invention will be understood more clearly with the aid of the further description which follows, which refers to examples illustrating the use of the NBL1 and 411 antigens, for the early immunodiagnosis of trichinellosis.

BRIEF DESCRIPTION OF THE DRAWINGS

FIG. 3: Comparison of the kinetics of appearance of anti-*Trichinella* antibodies detected by THX-NBL1 (Cterm) ELISA or by E/S Ag ELISA in sera from pigs infested with *T. spiralis*.
A: Detection by THX-NBL1 (Cterm) ELISA; B: detection by E/S Ag ELISA
Along the x-axis: number of days after infestation; along the y-axis: percentage reactivity. The detection threshold of the ELISAs is marked by a black line (44% for the THX-NBL1 (Cterm) ELISA and 14% for the E/S Ag ELISA). The mean and the standard deviations of the sample/positive control ratio are indicated for each group of infested pigs.

FIG. 5: Sequence of the THX-411 protein (SEQ ID NO: 25).
The sequence originating from 411 is indicated in bold characters. The sequences originating from the plasmid are indicated in italics.

FIG. 6: Immunoreactivity of the THX-411 protein.
1: positive serum 50 d pi; 2: positive serum 36 d pi; 3: negative serum −5 d; 4: conjugated control. M: molecular weight marker.

FIG. 7: Comparison of the kinetics of appearance of anti-*Trichinella* antibodies detected by THX-411 ELISA or by E/S Ag ELISA in sera from pigs infested with *T. spiralis*.
A: Detection by THX-411 ELISA; B: detection by E/S Ag ELISA
Along the x-axis: number of days after infestation; along the y-axis: percentage reactivity. The detection threshold of the ELISAs is marked by a black line (52% for the THX-411 ELISA and 14% for the E/S Ag ELISA). The mean and the standard deviations of the sample/positive control ratio are indicated for each group of infested pigs.

EXAMPLE 1

Production of the Recombinant THX-NBL1 (Cterm) Protein Containing a C-Terminal Portion of NBL1

Immunoscreening of a *Trichinella spiralis* L1NN cDNA library was carried out with a pig serum obtained 35 days after experimental infestation with 10 000 *T. spiralis* L1M. The sequencing of the clones recognized by this serum made it possible to determine that most of them encoded the same protein.

This protein is a putative serine protease, the cDNA sequence of which and the deduced amino acid sequence of which are respectively available on Genbank under numbers AF331160 and AAK16520, and are also reproduced here under the numbers SEQ ID NO: 1 and SEQ ID NO: 2. It is referred to herein as NBL1.

A portion of the C-terminal part of the protein was amplified using the oligonucleotides NBL1CtermF (5'-CAC-CGAAAATTCTCCTGAAGGA-3') (SEQ ID NO: 12) and NBL1CtermR (5'-TGTTGTTGTAGTAACTCC-3') (SEQ ID NO: 13) and the AccuPrime Pfx DNA polymerase (Invitrogen), and was cloned into the plasmid pET102D/topo using the "Champion pET102 Directional TOPO" expression kit according to the manufacturer's recommendations (Invitrogen).

Figures 1, 2:
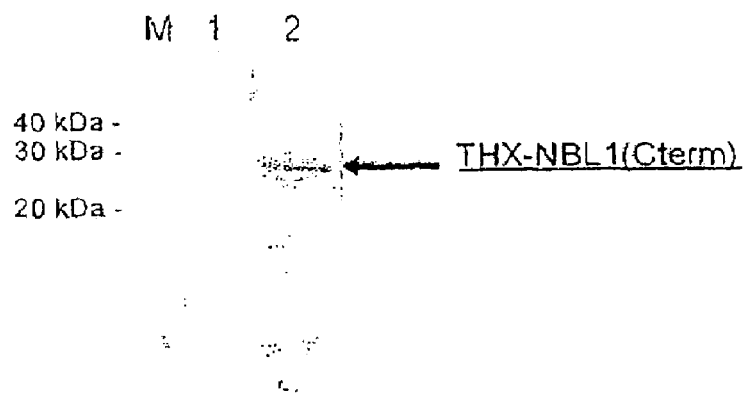
FIG. 1: Sequence of the THX-NBL1 (Cterm) protein (SEQ ID NO: 24).
The sequence originating from NBL1 is indicated in bold characters and the sequences originating from the plasmid pET102 are indicated in italics.
FIG. 2: Immunoreactivity of the THX-NBL1 (Cterm) protein.
M: Molecular weight marker; 1: negative pig serum; 2: serum from a pig experimentally infested with 20 000 L1M of *T. spiralis*.

The recombinant plasmid obtained, called pET102-NBL1 (Cterm), encodes a thioredoxin-NBL1 (Cterm) fusion protein (THX-NBL1 (Cterm)), of 291 AA, carrying a polyhistidine tag at the C-terminal position. The sequence of this fusion protein is represented in FIG. 1.

The THX-NBL1 (Cterm) fusion protein was expressed in *E. coli* BL21 Star (DE3), BL21 (DE3)pLys bacteria (Invitrogen) transformed with the plasmid pET102-NBL1 (Cterm), and purified by affinity chromatography under denaturing conditions on an Ni-NTA column (Ni-NTA spin columns kit; Ni-NTA beads), using the protocol recommended by the supplier (Qiagen).

The purified THX-NBL1 (Cterm) fusion protein appears, after electrophoresis under denaturing conditions (SDS-PAGE), in the form of a band at the expected size of 31.1 kDa.

The immunoreactivity of the THX-NBL1 (Cterm) protein with respect to a serum from a pig free of trichinellosis and from a serum of a pig infested with 20 000 *T. spiralis* L1M larvae, taken 60 days after infestation, was analyzed by Western blotting.

After electrophoresis under denaturing conditions (SDS-PAGE), the protein was electro-blotted onto a Hybond P (PVDF) membrane according to the supplier's instructions (Amersham). The membranes were prehybridized for 1 h in TBS-T (20 mM Tris-HCl, pH 7.5, 150 mM NaCl, 0.1% Tween 20) and 5% of skimmed milk. After 2 washes in TBS-T for 1 min, then 3 washes in TBS-T for 5 min, the membranes were incubated for 1 h with the pig serum diluted to 1/200 in TBS. After washing, the membranes were incubated for 20 min with the rabbit anti-pig IgG secondary antibody labeled with alkaline phosphatase (A1192, Sigma) diluted to 1/30

000, and then with the pure NBT/BCIP substrate (E116, Interchim) for 30 min in order to reveal the labeling.

The results are shown in FIG. 2.

A very strong immunoreactivity of THX-NBL1 (Cterm) is observed with the serum from the pig infested with *T. spiralis*.

EXAMPLE 2

Use of the THX-NBL1 (Cterm) for Detecting the Humoral Response Directed Against *Trichinella*

The THX-NBL1 (Cterm) protein, prepared as described in example 1 above, was evaluated by indirect ELISA with respect to sera derived from pigs infested with *Trichinella*, in comparison with the *T. spiralis* excretion/secretion (E/S) antigen.

The reference E/S antigen is prepared according to the protocol described by GAMBLE et al., (1988). It is obtained from the culture supernatant of L1M larvae maintained under survival conditions for 24 h in RPMI 1640 containing 1% of pyruvate, 15% of fetal calf serum (FCS), 1% of L-glutamine, 100 U/ml of penicillin and 100 μg/ml of streptomycin.

For the ELISA assays, the antigen diluted in 1×PBS buffer, at a rate of 1.25 μg/ml for the E/S antigen and of 2 μg/ml for THX-NBL1 (Cterm), is incubated overnight at 4° C. on 96-well plates (MediSorp plates, NUNC). After washes (1×PBS, Tween 20 at 0.05%), the plates are saturated at ambient temperature for 1 H with a solution of skimmed milk diluted to 2% in the washing solution.

100 μl of pig serum diluted to 1/20 in 1×PBS buffer, supplemented with Tween 20 at 0.05%, are deposited into each well. After incubation for 30 minutes at 37° C., followed by 3 washes (1×PBS, Tween 20 at 0.05%), 100 μl of the solution of conjugate (protein G-peroxidase (P-8170, Sigma)) diluted to 1/32 000 in 1×PBS buffer, supplemented with Tween 20 at 0.05%, are deposited into each well. After further incubation for 30 min at 37° C., followed by 3 washes (1×PBS, Tween 20 at 0.05%), 100 μl of a solution of substrate (3,3',5,5'-tetramethylbenzidine-hydrogen peroxide: TMB3) are deposited into each well. After incubation for 20 min at ambient temperature in the dark, the reaction is stopped by adding 100 μl/well of 0.5 M $H_2SO_4$. The plates are read by measuring the absorbance at 450 nm.

The result of the ELISA plate readings is provided in the form of the percentage reactivity of a sample serum relative to a positive control serum.

$$\% \frac{S}{p} = (OD \text{ sample} - OD \text{ negative control}/OD \text{ positive control} - OD \text{ negative control}) \times 100$$

The positivity threshold (equal to twice the mean value of the reference negative samples) is 14% for the E/S Ag ELISA and 44% for the THX-NBL1 (Cterm) ELISA.

The kinetics of appearance of the anti-*Trichinella* antibodies detected by THX-NBL1 (Cterm) ELISA or by E/S Ag ELISA in sera from conventional pigs experimentally infested with 200, 1000 or 20 000 *T. spiralis* L1M larvae were compared.

The results are given in FIG. 3.

The THX-NBL1 (Cterm) antigen allows the dose-dependent detection of humoral responses directed against *T. spiralis*. The detection of conformational epitopes by means of this ELISA assay combined with the detection of linear epitopes by means of Western blotting demonstrate, moreover, the immunodominant nature of the *Trichinella* NBL1 protein.

The THX-NBL1 (Cterm) ELISA detects the seroconversion from the 25th day pi onward, whereas the E/S Ag ELISA detects the seroconversion only 10 days later.

The detection, by E/S Ag ELISA and THX-NBL1 (Cterm) ELISA, of the humoral responses induced by *T. spiralis* and the other three species of *Trichinella* identified in Europe, *T. nativa, T. britovi* and *T. pseudospiralis*, was also compared.

The results are summarized in table I below.

TABLE I

| Trichinella species | Inoculum (a). | Infectivity (b). | Total Screening rate by E/S Ag ELISA | Total Screening rate by E/S Ag ELISA | Screening rate by THX-NBL1 (Cterm) ELISA | Total Screening rate by THX-NBL1 (Cterm) ELISA | Number of animals codetected later by THX-NBL1 (Cterm) ELISA | Number of animals detected at the same time by the 2 ELISA assays | Number of animals detected earlier by THX-NBL1 (Cterm) ELISA | Number of animals detected at the same time by the 2 ELISA assays or earlier by THX-NBL1 (Cterm) ELISA | Gain in early detection induced by THX-NBL1 (Cterm) ELISA (c) |
|---|---|---|---|---|---|---|---|---|---|---|---|
| *T. spiralis* | 200 | 3 | 3/3 | 9/9 | 1/3 | 7/9 | — | — | 7/7 | 7/7 | 5-20 |
| | 1000 | 43.1 | 3/3 | | 3/3 | | | | | | |
| | 20000 | 538.9 | 3/3 | | 3/3 | | | | | | |
| *T. britovi* | 200 | 1.8 | 1/3 | 7/9 | 1/3 | 6/9 | — | — | 6/6 | 6/6 | 5-45 |
| | 1000 | 1 | 3/3 | | 2/3 | | | | | | |
| | 20000 | 123.1 | 3/3 | | 3/3 | | | | | | |
| *T. nativa* | 200 | 0.0007 | 1/3 | 5/9 | 1/3 | 6/9 | — | — | 6/6 | 6/6 | 15-30 |
| | 1000 | 0.0015 | 1/3 | | 2/3 | | | | | | |
| | 20000 | 0.1022 | 3/3 | | 3/3 | | | | | | |
| *T. pseudospiralis* | 200 | 0.058 | 0/3 | 6/9 | 0/3 | 5/9 | — | — | 5/5 | 5/5 | 5-45 |
| | 1000 | 2.1 | 3/3 | | 2/3 | | | | | | |
| | 20000 | 98.9 | 3/3 | | 3/3 | | | | | | |

(a) Infectious inoculum in number of *Trichinella* L1M per pig
(b) Mean muscle parasite load per animal (in larvae per gram of muscle)
(c) Gain in early detection expressed in days, obtained with the NBL1(Cterm) ELISA assay compared with the E/S Ag ELISA assay in the animals codetected by these 2 assays.

All these results show that the THX-NBL1 (Cterm) ELISA allows a particularly early detection of the humoral responses, from the 15th day pi onward, for the highly infested animals, and a slightly delayed detection for the animals infested with a medium load of 1000 L1M (25th day pi). Similar results were obtained with holoxenic pigs infested according to the same protocol. The earliest seroconversion detected by the E/S Ag ELISA was at the 25th day pi. The comparison of the results obtained with the 2 ELISA assays demonstrated a gain of 5 to 20 days in terms of early detection for the diagnosis of T. spiralis by using the THX-NBL1 (Cterm) ELISA (table I). Furthermore, the animals infested with T. spiralis which were diagnosed both by the E/S Ag ELISA and the THX-NBL1 (Cterm) ELISA all saw their window of serological detection reduced with the THX-NBL1 (Cterm) ELISA. The sensitivity of the THX-NBL1 (Cterm) ELISA was demonstrated with the effect of screening of 7/9 conventional pigs during this animal experiment, i.e. 3/3 pigs infested with 20 000 L1M, 3/3 pigs infested with 1000 L1M and 1/3 pigs infested with only 200 L1M of T. spiralis. The detections were associated with the T. spiralis muscle parasite load in these animals, which varied on average from 3 larvae per gram (LpG) for the pigs experimentally infested with 200 L1M, to 43 LpG for the pigs experimentally infested with 1000 L1M, and 538 LpG for the pigs experimentally infested with 20 000 L1M.

The humoral responses induced by the other three species of Trichinella identified in Europe, T. nativa, T. britovi and T. pseudospiralis, were themselves also detected in a dose-dependent manner by the THX-NBL1 (Cterm) ELISA, demonstrating the genetic and antigenic conservation of NBL1 in the Trichinella genus (immunodominance) and, consequently, the great advantage thereof for the broad-spectrum diagnosis of trichinelloses. The sensitivity and the earliness of the diagnosis (15th day pi) were confirmed. The seroconversion window was reduced by 5 to 45 days with the THX-NBL1 (Cterm) ELISA, and, like the infestation with T. spiralis, all the animals which were diagnosed both by E/S Ag ELISA and THX-NBL1 (Cterm) ELISA saw their serological detection window reduced with the THX-NBL1 (Cterm) ELISA. Furthermore, the analysis of the infestation with the T. nativa species demonstrates the high sensitivity of the THX-NBL1 (Cterm) ELISA, which diagnosed 6/9 animals (against 5/9 animals with the E/S Ag ELISA), including 2 pigs not revealed by screening with the E/S Ag ELISA, whereas the muscle parasite load was on average only $7 \times 10^{-4}$, at 0.1 LpG only.

The specificity of the THX-NBL1 (Cterm) ELISA was demonstrated by means of the sera taken from all the animals before each experimental infestation and up to 10 days pi. More than 200 sera from free range pigs were used to show the specificity of the molecule. No pig negative with respect to Trichinella reacts with the THX-NBL1 (Cterm) ELISA.

Figure 4:
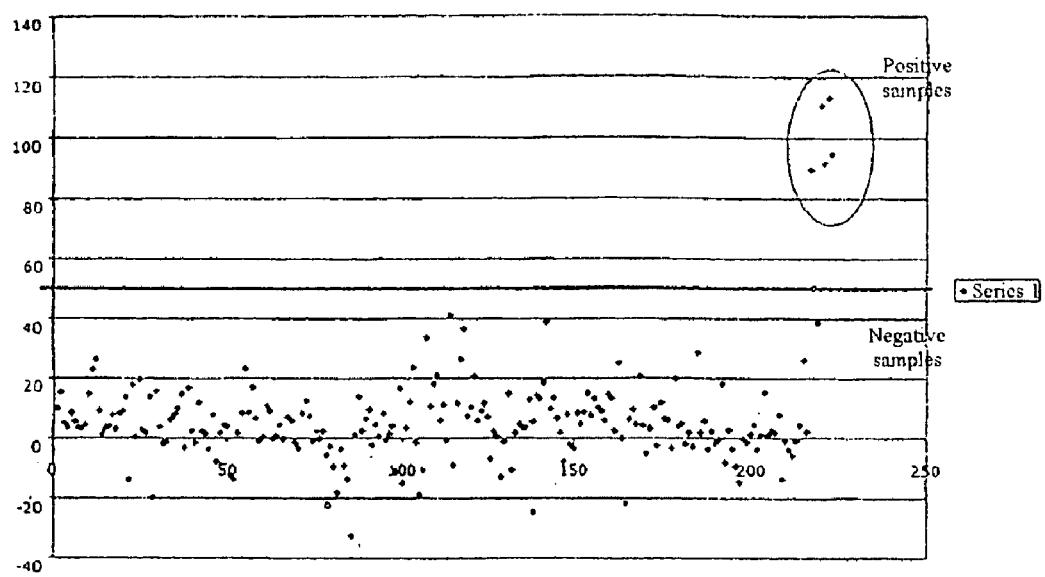
FIG. 4: Specificity of the NBL1 (Cterm) ELISA.
Along the x-axis: cohort of 230 negative samples originating from factory-farmed pigs or from free range pigs. The 5 positive samples originate from sera of experimentally infested pigs. The threshold is equal to twice the mean value of the negative samples. Along the y-axis: percentage reactivity.

These results are given in FIG. 4

EXAMPLE 3

Identification of an Immunodominant Epitope of NBL1

An analysis, in silico, of the deduced amino acid sequence of the C-terminal part of NBL1 was carried out in order to predict the most antigenic regions.

The results of the analysis in silico resulted in the selection of 11 overlapping peptides covering 113 Am of the c-terminal part of NBL1 (from AA 327 to AA 440). The sequences of these peptides are indicated hereinafter

```
N5EM1:
NH2- NSPEGTVKWASKEDS -COHN2      (SEQ ID NO: 14)

N5EM2:
NH2- ASKEDSPVDLSTASR -COHN2      (SEQ ID NO: 15)

N5EM3:
NH2- LSTASRPTNPYTGSR -COHN2      (SEQ ID NO: 16)

N5EM4:
NH2- PYTGSRPTSPSSGSR -COHN2      (SEQ ID NO: 17)

N5EM5:
NH2- PSSGSRPTYPSSGSR -COHN2      (SEQ ID NO: 6)

N5EM6:
NH2- PSSGSRPTSPSSGSR -COHN2      (SEQ ID NO: 18)

N5EM7:
NH2- PSSGSRPTYPYTGSR -COHN2      (SEQ ID NO: 7)

N5EM8:
NH2- PYTGSRPTPQKPVFP -COHN2      (SEQ ID NO: 19)

N5EM9:
NH2- QKPVFPSYQKYPPAV -COHN2      (SEQ ID NO: 20)

N5EM10:
NH2- KYPPAVQKYIDSLPS -COHN2      (SEQ ID NO: 21)

N5EM11:
NH2- RPTSPSSGSRPTYPS -COHN2      (SEQ ID NO: 8)
```

The antigenicity of the N5EM peptides with respect to a serum from a pig infested with 20 000 T. spiralis L1M larvae, collected 60 days after the infestation, was evaluated by indirect ELISA using a protocol identical to that described in example 2, with the exception that the peptides, biotinylated beforehand, are incubated (2 µg/ml in 1×PBS; 100 µl/well) on plates pretreated with streptavidin.

Three immunoreactive peptides (NSEM5, 7 and 11) were detected. The analysis of the primary sequence of the immunoreactive peptides revealed the presence of a common motif of 10 amino acids (PSSGSRPTYP) (SEQ ID NO: 5). This motif is, moreover, present 4 times over the entire sequence of the NBL1 protein. Furthermore, the mapping of epitopes via overlapping peptides of 6AA made it possible to demonstrate the essential importance of a single AA, a tyrosine, for the immunoreactivity of the linear epitope within the peptides.

Additional experiments finally demonstrated that N5EM11 was the most reactive peptide compared to N5EM5 and N5EM7, in terms of sensitivity and earliness.

This peptide was compared with the E/S antigen of T. spiralis, as described in example 2 for THX-NBL1 (Cterm).

The results are summarized in table II below.

TABLE II

| Trichinella species | Inoculum (a) | Infectivity (b) | Screening rate by E/S Ag ELISA | Total screening rate by E/S Ag ELISA | Screening rate by N5EM11 ELISA | Total screening rate by N5EM11 ELISA | Number of animals codetected later by N5EM11 ELISA | Number of animals detected at the same time by the 2 ELISA assays | Number of animals detected earlier by N5EM11 ELISA | Number of animals detected at the same time by the 2 ELISA assays or earlier by N5EM11 ELISA | Gain in early detection induced by N5EM11 ELISA (c) |
|---|---|---|---|---|---|---|---|---|---|---|---|
| T. spiralis | 200 | 3 | 3/3 | 9/9 | 0.3 | 5/9 | — | 2/5 | 3/5 | 5/5 | 5-10 |
|  | 1000 | 43.1 | 3/3 |  | 2/3 |  |  |  |  |  |  |
|  | 20000 | 538.9 | 3/3 |  | 3/3 |  |  |  |  |  |  |
| T. britovi | 200 | 1.8 | 1/3 | 7/9 | 1/3 | 5/9 | — | 1/5 | 4/5 | 5/5 | 5-30 |
|  | 1000 | 1 | 3/3 |  | 1/3 |  |  |  |  |  |  |
|  | 20000 | 123.1 | 3/3 |  | 3/3 |  |  |  |  |  |  |
| T. nativa | 200 | 0.0007 | 1/3 | 5/9 | 0/3 | 4/9 | — | — | 4/4 | 4/4 | 15-25 |
|  | 1000 | 0.0015 | 1/3 |  | 1/3 |  |  |  |  |  |  |
|  | 20000 | 0.1022 | 3/3 |  | 3/3 |  |  |  |  |  |  |
| T. pseudospiralis | 200 | 0.058 | 0/3 | 6/9 | 0/3 | 4/9 | 2/4 | — | 2/4 | 2/4 | 30 |
|  | 1000 | 2.1 | 3/3 |  | 2/3 |  |  |  |  |  |  |
|  | 20000 | 98.9 | 3/3 |  | 2/3 |  |  |  |  |  |  |

(a) Infectious inoculum in number of *Trichinella* L1M per pig.
(b) Mean muscle parasite load per animal (in larvae per gram of muscle)
(c) Gain in early detection expressed in days, obtained with the N5EM11 ELISA assay compared with the E/S Ag ELISA assay in the animals codetected by these 2 assays.

These results show that the N5EM11 ELISA makes it possible to detect moderate *T. spiralis* infestations. Furthermore, early detection from the 20th day after infection onward was obtained, i.e. 5 to 10 days earlier than what was possible with the E/S Ag ELISA.

A decrease in the anti-N5EM11 antibody titer after the detection peak was also observed, which confirms this early nature, and which is of use for dating a recent infestation. All the pigs infested with *T. spiralis* and diagnosed using the N5EM11 peptide ELISA show a seroconversion window which is in part similar but, in the majority of cases, smaller than that observed with the E/S Ag ELISA.

Moreover, N5EM11 exhibits antigen cross reactions with the serum from pigs infested with *T. nativa*, *T. britovi* and *T. pseudospiralis*, demonstrating the immunodominance of this peptide at the L1NN stage of *Trichinella*. These antigen cross reactions result in detection that can be obtained 5 to 30 days earlier than with the E/S Ag ELISA.

A decrease in sensitivity was nevertheless noted in comparison with the E/S Ag ELISA in terms of delayed detection for animals infected with *T. pseudospiralis* and codetected using the two assays. In contrast, the N5EM11 ELISA also made it possible to diagnose an animal infested with *T. nativa* and not detected by screening with the E/S Ag ELISA, although the muscle parasite load was residual.

The specificity of the N5EM11 ELISA was evaluated using sera taken from 300 animals before experimental infestation and up to 10 days pi. This specificity is greater than 99% (results not shown).

EXAMPLE 4

Identification and Isolation of the 411 Antigen

The 411 cDNA clone was selected from a cDNA library of the early invasive Ad+L1NN stages of *T. spiralis*.

The nucleic sequence of this cDNA clone, and also the deduced polypeptide sequence, were determined and are respectively represented in the sequence listing under the numbers SEQ ID NO: 3 and SEQ ID NO: 4. The open reading frame of 411 encodes a putative protein of 20 kDa. With the exception of a signal peptide, no protein domain was identified.

Comparison of the complete open reading frame of 411 with the sequences available on Genbank shows that it has 78.7% identity with the Tp21-3 excretion/secretion protein identified in *T. pseudospiralis* (AAF79206; NAGANO et al., 2001), and 86.6% identity with the hypothetical ORF 17.20 sequence of *T. spiralis* submitted by Polvere and Despommier (AAB48489). These sequence comparisons identify 411 as a new member of this gene family common to the *Trichinella* genus.

The complete open reading frame of 411 was amplified using the oligonucleotides 411F (5'-CACCCGAGAAAA-CATGCAT-3') (SEQ ID NO: 22) and 411R (5'-TCCAT-TCAATTTTGCGTCAC-3') (SEQ ID NO: 23), and the AccuPrime Pfx DNA polymerase (Invitrogen), and was cloned into the plasmid pET102D/topo, using the "Champion pET102 Directional TOPO" expression kit according to the manufacturer's recommendations (Invitrogen).

The recombinant plasmid obtained, for pET102-411, encodes a thioredoxin-411 fusion protein (THX-411) of 330 AA, for a predicted molecular mass of 36.7 kDa, and carrying a polyhistidine tag at the C-terminal position. The sequence of this fusion protein is given in FIG. 5.

The THX-411 fusion protein was expressed in *E. coli* BL21 Star (DE3), BL21 (DE3)pLys bacteria (Invitrogen) transformed by the plasmid pET102-411, and purified by affinity chromatography under denaturing conditions on an Ni-NTA column (Ni-NTA spin columns kit; Ni-NTA beads), using the protocol recommended by the supplier (Qiagen).

The purified THX-411 fusion protein appears, after electrophoresis under denaturing conditions (SDS-PAGE) in the form of a band at the expected size of 36.7 kDa.

The immunoreactivity of the THX-411 protein with respect to a serum from a pig free of trichinellosis, and to the serum from the same pig, 30 days and 50 days after infestation with 20 000 *T. spiralis* L1M larvae, was compared with that of the E/S reference antigen (prepared as described in example 2 above). The analysis was carried out by Western blotting, using the same protocol as that described in example 1 above.

The results are given in FIG. 6.

Very strong immunoreactivity of THX-411 with the sera from the pig infested with *T. spiralis* and the early detection of anti-411 antibodies (30 days pi) were observed. A slight background noise was observed due to the cross reactions between the residual high-molecular-weight bacterial proteins remaining in the THX-411 preparation and the anti-*E. coli* antibodies present in the sera.

EXAMPLE 5

Use of THX-411 for Detecting the Humoral Response Directed Against *Trichinella*

The protein, prepared as described in example 4 above, was evaluated by indirect ELISA with respect to sera derived from pigs infested with *Trichinella*, in comparison with the excretion/secretion (E/S) antigen of *T. spiralis*.

The kinetics of appearance of the anti-*Trichinella* antibodies detected by THX-411 ELISA or by E/S Ag ELISA in sera from conventional pigs experimentally infested with 200, 1000 or 20 000 *T. spiralis* L1M larvae were compared. The detection, by E/S Ag ELISA and THX-411 ELISA, of the humoral responses induced by *T. spiralis* and the other three species of *Trichinella* identified in Europe, *T. native, T. britovi* and *T. pseudospiralis*, was also compared.

The protocol used is identical to that described in example 2. The THX-411 antigen was used at 2 μg/ml, and the E/S antigen at 1.25 μg/ml.

The positivity threshold is 14% for the E/S Ag ELISA and 52% for the THX-411 ELISA.

The results are given in FIG. 7, and also in table III below.

The recombinant THX-411 protein allows a particularly early detection of antibodies directed against *T. spiralis* (from the 20th day pi onward for the animals highly infested with 20 000 L1M). The seroconversion is accompanied by a profile of humoral responses having high titers and maintained for up to 60 days pi. The seroconversion of the animals infested with a moderate and low load of the parasite was detected later, at the 30th day pi and 60th day pi, respectively. The earliest seroconversion detected by the E/S Ag ELISA is at the 25th day pi.

Two out of five of the *T. spiralis*-infested animals which were diagnosed with both the E/S Ag ELISA and the THX-411 ELISA saw their window of serological detection get smaller with the THX-411 ELISA, with a gain of 5 to 10 days in terms of earliness. The sensitivity of the THX-411 ELISA was demonstrated with the effective screening of 5/9 conventional pigs during this animal experiment, i.e. 3/3 pigs infested with 20 000 L1M, 1/3 pigs infested with 1000 L1M and 1/3 pigs infested with only 200 L1M of *T. spiralis*. The detections were associated with the *T. spiralis* muscle parasite load in these animals, which varied on average from 3 larvae per gram (LpG) for the pigs experimentally infested with 200 L1M, to 43 LpG for the pigs infested with 1000 L1M, and 538 LpG for the pigs infested with 20 000 L1M.

The humoral responses induced by *T. nativa, T. britovi* and *T. pseudospiralis* were themselves also detected with the THX-411 ELISA (10/12 animals infested with 20 000 L1M), demonstrating the genetic and antigenic conservation of 411 in the *Trichinella* genus and, consequently, its absolute advantage for the broad-spectrum diagnosis of trichinelloses. The earliness of the diagnosis was confirmed from the 20th day pi onward. The seroconversion window was reduced by 5 to 20 days with the 411 ELISA, and, like the infestation with the *T. spiralis*, 50% to 100% of the animals which were

TABLE III

| Trichinella species | Inoculum (a). | Infectivity (b). | Screening rate by E/S Ag ELISA | Total screening rate by E/S Ag ELISA | Screening rate by THX-411 ELISA | Total screening rate by THX-411 ELISA | Number of animals codetected later by THX-411 ELISA | Number of animals detected at the same time by the 2 ELISA assays | Number of animals detected earlier by THX-411 ELISA | Number of animals detected at the same time by the 2 ELISA assays or earlier by THX-411 ELISA | Gain in early detection induced by THX-411 ELISA (c) |
|---|---|---|---|---|---|---|---|---|---|---|---|
| T. spiralis | 200 | 3 | 3/3 | 9/9 | 1.3 | 5/9 | 2/5 | 1/5 | 2/5 | 3/5 | 5-10 |
|  | 1000 | 43.1 | 3/3 |  | 2/3 |  |  |  |  |  |  |
|  | 20000 | 538.9 | 3/3 |  | 3/3 |  |  |  |  |  |  |
| T. britovi | 200 | 1.8 | 1/3 | 7/9 | 0/3 | 4/9 | — | — | 4/4 | 4/4 | 5-20 |
|  | 1000 | 1 | 3/3 |  | 2/3 |  |  |  |  |  |  |
|  | 20000 | 123.1 | 3/3 |  | 2/3 |  |  |  |  |  |  |
| T. nativa | 200 | 0.0007 | 1/3 | 5/9 | 1/3 | 6/9 | — | 1/6 | 5/6 | 6/6 | 10-20 |
|  | 1000 | 0.0015 | 1/3 |  | 2/3 |  |  |  |  |  |  |
|  | 20000 | 0.1022 | 3/3 |  | 3/3 |  |  |  |  |  |  |
| T. pseudo-spiralis | 200 | 0.058 | 0/3 | 6/9 | 0/3 | 2/9 | 1/2 | — | 1/2 | 1/2 | 20 |
|  | 1000 | 2.1 | 3/3 |  | 0/3 |  |  |  |  |  |  |
|  | 20000 | 98.9 | 3/3 |  | 2/3 |  |  |  |  |  |  |

(a) Infectious inoculum in number of *Trichinella* LIM per pig.
(b) Mean muscle parasite load per animal (in larvae per gram of muscle)
(c) Gain in early detection expressed in days, obtained with the 411 ELISA assay compared with the E/S Ag ELISA assay in the animals codetected by these 2 assays.

All these results show that the 411 antigen allows the dose-dependent detection of the humoral responses directed against *T. spiralis*. The detection of conformational epitopes using this ELISA assay combined with the detection of linear epitopes with Western blotting demonstrate, moreover, the immunodominant nature of the *Trichinella* 411 protein.

diagnosed with both the E/S Ag ELISA and the THX-411 ELISA saw their serological detection window get smaller with the THX-411 ELISA. The analysis of the infestation with the *T. nativa* species demonstrated an increased sensitivity of the THX-411 ELISA, which diagnosed 6/9 animals (against 5/9 animals with the E/S Ag ELISA), although the muscle parasite load was on average only 7×10⁻⁴, at 0.1 LpG only. Furthermore, similar humoral response profiles were obtained for the animals infested with *T. spiralis* and *T. nativa*, although the intensity of the infestation generated by the latter species was significantly lower, suggesting that the 511 protein of *T. nativa* is very highly immunogenic in nature and could be used for the detection of this species resistant to freezing.

The specificity of the THX-411 ELISA was evaluated using sera taken from 150 animals before experimental infestation and up to 10 days pi. This specificity is greater than 99% (results not shown).

CONCLUSION

The NBL1 and 411 antigens constitute immunodominant antigens which are conserved within the *Trichinella* genus. The ELISA assays using these antigens (NBL1 C-terminal part; N5EM11 peptide epitope of NBL1; 411 antigen) have a greater than 99% specificity with respect to *Trichinella*, and allow the early diagnosis (15-60 days after infestation) of porcine trichinelloses produced by the four species of *Trichinella* identified in Europe.

The ELISA assay using the purified recombinant THX-NBL1 (Cterm) protein, containing the immunodominant epitope of NBL1 located in the C-terminal part of the protein, is *Trichinella*-specific, and sensitive, and allows the diagnosis of porcine trichinelloses from 5 to 45 days earlier than with the E/S Ag ELISA. Furthermore, this assay made it possible to obtain a reduced serological detection window compared with the E/S Ag ELISA in 100% of the animals which were diagnosed both with the E/S Ag ELISA and with the THX-NBL1 (Cterm), The ELISA assay using the purified recombinant THX-411 protein reproduces the kinetics of the humoral responses detected with the E/S Ag ELISA, with a sensitivity that is currently slightly lower (17/36 animals diagnosed). However, the sensitivity of this new ELISA made it possible to diagnose one pig not diagnosed by screening with the E/S Ag ELISA. The THX-411 ELISA can make it possible to diagnose porcine trichinelloses from 5 to 20 days earlier than with the E/S Ag ELISA. Furthermore, 50% to 100% of the animals which were diagnosed both with the E/S Ag ELISA and the THX-411 ELISA saw their serological detection window get smaller with the THX-411 ELISA.

All these results show that the NBL1 and 411 antigens can be used, as an alternative to the E/S antigen, or as a supplement thereto, for the early serological diagnosis of trichinelloses. In addition, the combination of these two new *Trichinella* antigens makes it possible to enhance the sensitivity of the ELISA, by virtue of the diagnosis of an additional animal.

The combination of NBL1 (Cterm) with immunodominant peptide of N5EM11 type, and 411 makes it possible to enhance the sensitivity of *Trichinella* diagnosis (24/36 animals detected).

The additive effect of NBL1 with 411 is reflected by the gain in detection of one animal, induced with 411, and also by the earlier detection of one animal, induced with 411. The triple combination (NBL1, 411, N5EM11) stabilizes the ELISA assay over time through the simultaneous codetection of antibodies by 2 or 3 antigens, without, however, any additional gain in terms of number of animals.

On the other hand, the early diagnosis, <30 days pi, was obtained by virtue of the two antigens NBL1 and 411.

REFERENCES

MURRELL et al., The systematics of the genus *Trichinella* with a key to species, Vet Parasitol, 93, 293-307, (2000).
GASSER et al., Nonisotopic single-strand conformation polymorphism analysis of sequence variability in ribosomal DNA expansion segments within the genus *Trichinella* (Nematoda: Adenophorea), Electrophoresis, 25, 3357-3364, (2004).
BOIREAU et al., Risques parasitaires liés aux aliments d'origine animale [Parasitic risks linked to feeds of animal origin], French laboratory review, 71-89, (2002).
CAPO & DESPOMMIER, Clinical aspects of infection with *Trichinella* spp, Clin Microbiol Rev, 9, 47-54, (1996).
FOURESTIE et al., Randomized trial of albendazole versus tiabendazole plus flubendazole during an outbreak of human trichinellosis, Parasitol Res, 75, 36-41, (1988).
DUPOUY-CAMET, Trichinellosis: a worldwide zoonosis, Vet Parasitol, 93, 191-200, (2000).
MURRELL & POZIO, Trichinellosis: the zoonosis that won't go quietly, Int J Parasitol, 30, 1339-1349, (2000).
BOIREAU et al., *Trichinella* in horses: a low frequency infection with high human risk, Vet Parasitol, 93, 309-320, (2000).
GAMBLE et al., Diagnosis of swine trichinosis by enzyme-linked immunosorbent assay (ELISA) using an excretory-secretory antigen, Vet Parasitol, 13, 349-361, (1983).
GAMBLE et al., Evaluation of excretory-secretory antigens for the serodiagnosis of swine trichinellosis, Vet Parasitol, 30, 131-137, (1988).
REASON et al., Novel tyvelose-containing tri- and tetra-antennary N-glycans in the immunodominant antigens of the intracellular parasite *Trichinella spiralis*, Glycobiology, 4, 593-603, (1994).
NAGANO et al., Molecular cloning and characterization of a 21 kDa protein secreted from *Trichinella pseudospiralis*, J Helminthol, 75, 273-278, (2001)

The invention claimed is:

1. A method for detecting antibodies induced by *Trichinella* infestation in a biological sample, comprising contacting said sample with an antigenic polypeptide recognized by said antibodies, wherein said polypeptide comprises an immunodominant epitope of the NBL1 antigen, wherein said epitope comprises the sequence PSSGSRPTYP (SEQ ID NO: 5), wherein the polypeptide does not include the entire sequence of newborn larvae-specific serine protease SS2 or newborn larvae-specific serine protease SS2-1.

2. The method of claim 1, wherein said polypeptide is included in a mixture comprising one or more polypeptide(s) comprising amino acids 25-175 of the sequence SEQ ID NO: 4 or comprising a sequence having at least 70% identity with the sequence of amino acids 25-175 of the sequence SEQ ID NO: 4.

3. A method for detecting the presence of antibodies induced by *Trichinella* infestation in a biological sample comprising:
   a. bringing said biological sample into contact with an antigenic polypeptide comprising an immunodominant epitope of the NBL1 antigen comprising the sequence PSSGSRPTYP (SEQ ID NO: 5) under conditions which allow the formation of an antigen/antibody complex with the antibodies induced by *Trichinella* infestation present in said sample, wherein the polypeptide does not include the entire sequence of newborn larvae-specific serine protease SS2 or newborn larvae-specific serine protease SS2-1; and
   b. detecting the antigen/antibody complex formed.

4. The method of claim 2, wherein the one or more polypeptides comprises a sequence having at least 90% identity with the sequence of amino acids 25-175 of the sequence SEQ ID NO: 4.

5. The method of claim 2, wherein the one or more polypeptides comprises a sequence having at least 95% identity with the sequence of amino acids 25-175 of the sequence SEQ ID NO: 4.

6. The method of claim 2, wherein the one or more polypeptides comprises amino acids 25-175 of the sequence SEQ ID NO: 4.

7. The method of claim 3, wherein said polypeptide is included in a mixture comprising one or more polypeptide(s) comprising amino acids 25-175 of the sequence SEQ ID NO: 4 or comprising a sequence having at least 70% identity with the sequence of amino acids 25-175 of the sequence SEQ ID NO: 4.

8. The method of claim 7, wherein the one or more polypeptides comprises a sequence having at least 90% identity with the sequence of amino acids 25-175 of the sequence SEQ ID NO: 4.

9. The method of claim 7, wherein the one or more polypeptides comprises a sequence having at least 95% identity with the sequence of amino acids 25-175 of the sequence SEQ ID NO: 4.

10. The method of claim 7, wherein the one or more polypeptides comprises amino acids 25-175 of the sequence SEQ ID NO: 4.

11. The method of claim 1, wherein the antigenic polypeptide comprising the sequence PSSGSRPTYP (SEQ ID NO: 5) is
   (a) a polypeptide comprising the sequence of amino acids 363-409 of SEQ ID NO: 2; or
   (b) a fragment of polypeptide (a) comprising the sequence PSSGSRPTYP (SEQ ID NO: 5).

12. The method of claim 11, wherein said fragment of polypeptide (a) comprises the polypeptide sequence PSSGSRPTYPSSGSR (SEQ ID NO: 6), PSSGSRPTYPYTGSR (SEQ ID NO: 7), or RPTSPSSGSRPTYPS (SEQ ID NO: 8).

13. The method of claim 11, wherein said antigenic polypeptide is fused to one or more other heterologous sequence(s).

14. The method of claim 3, wherein the antigenic polypeptide comprising the sequence PSSGSRPTYP (SEQ ID NO: 5) is
   (a) a polypeptide comprising the sequence of amino acids 363-409 of SEQ ID NO: 2; or
   (b) a fragment of polypeptide (a) comprising the sequence PSSGSRPTYP (SEQ ID NO: 5).

15. The method of claim 14, wherein said fragment of polypeptide (a) comprises the polypeptide sequence PSSGSRPTYPSSGSR (SEQ ID NO: 6), PSSGSRPTYPYTGSR (SEQ ID NO: 7), or RPTSPSSGSRPTYPS (SEQ ID NO: 8).

16. The method of claim 14, wherein said antigenic polypeptide is fused to one or more other heterologous sequence(s).

17. The method of claim 1, wherein the method is capable of detecting antibodies induced by *Trichinella* infestation of more than one species.

18. The method of claim 17, wherein the species is *T. spiralis, T. nativa, T. britovi, T. pseudospiralis*, and combinations thereof.

19. The method of claim 3, wherein the method is capable of detecting antibodies induced by *Trichinella* infestation of more than one species.

20. The method of claim 19, wherein the species is *T. spiralis, T. nativa, T. britovi, T. pseudospiralis*, and combinations thereof.

21. The method of claim 1, wherein the antibodies are detected within 30 days of said infestation.

22. The method of claim 1, wherein the antibodies are detected within 25 days of said infestation.

23. The method of claim 1, wherein the antibodies are detected within 20 days of said infestation.

24. The method of claim 1, wherein the antibodies are detected within 15 days of said infestation.

25. The method of claim 3, wherein the antibodies are detected within 30 days of said infestation.

26. The method of claim 3, wherein the antibodies are detected within 25 days of said infestation.

27. The method of claim 3, wherein the antibodies are detected within 20 days of said infestation.

28. The method of claim 3, wherein the antibodies are detected within 15 days of said infestation.

29. The method of claim 6, wherein the antibodies are detected within 20 days of said infestation.

30. The method of claim 6, wherein the antibodies are detected within 15 days of said infestation.

31. The method of claim 10, wherein the antibodies are detected within 20 days of said infestation.

32. The method of claim 10, wherein the antibodies are detected within 15 days of said infestation.

33. A method for detecting antibodies induced by *Trichinella* infestation in a biological sample, comprising contacting said sample with an antigenic polypeptide recognized by said antibody, wherein said antigenic polypeptide comprises an immunodominant epitope of the NBL1 antigen, wherein said epitope comprises the sequence PSSGSRPTYP (SEQ ID NO: 5), wherein the polypeptide does not include the entire sequence of SEQ ID NO: 2 or Genbank Accession Number AAR36900.

34. A method for detecting antibodies induced by *Trichinella* infestation in a biological sample, comprising contacting said sample with an antigenic polypeptide recognized by said antibody, wherein said antigenic polypeptide comprises a sequence having at least 90% identity with the sequence of amino acids 25-175 of the sequence SEQ ID NO: 4.

35. The method of claim 34, wherein the polypeptide comprises a sequence having at least 95% identity with the sequence of amino acids 25-175 of the sequence SEQ ID NO: 4.

36. The method of claim 34, wherein the one or more polypeptides comprises amino acids 25-175 of the sequence SEQ ID NO: 4.

* * * * *

SEQUENCE LISTING

<160> NUMBER OF SEQ ID NOS: 25

<210> SEQ ID NO 1
<211> LENGTH: 1609
<212> TYPE: DNA
<213> ORGANISM: Trichinella spiralis
<220> FEATURE:
<221> NAME/KEY: CDS
<222> LOCATION: (90)..(1487)

<400> SEQUENCE: 1

| | |
|---|---:|
| gaaaagtgcc gctttgtttc aaagacaaat agaaatgaaa caaaggatat tccatacgaa | 60 |

| | | | | | | | | | | | | | | | | |
|---|---|---|---|---|---|---|---|---|---|---|---|---|---|---|---|---:|
| cagtagccat taaaaggtgt gctgcatgc | | | atg<br>Met<br>1 | cat<br>His | aaa<br>Lys | att<br>Ile | aca<br>Thr<br>5 | cac<br>His | aaa<br>Lys | agt<br>Ser | | | | | | 113 |
| att<br>Ile | gta<br>Val<br>10 | tca<br>Ser | cgt<br>Arg | cat<br>His | aca<br>Thr<br>15 | ttt<br>Phe | gct<br>Ala | gtt<br>Val | tat<br>Tyr | ttg<br>Leu<br>20 | tta<br>Leu | gtt<br>Val | agt<br>Ser | ggt<br>Gly | cag<br>Gln | 161 |
| aaa<br>Lys<br>25 | ctg<br>Leu | caa<br>Gln | tat<br>Tyr | ata<br>Ile<br>30 | tat<br>Tyr | ata<br>Ile | ttt<br>Phe | att<br>Ile | tgc<br>Cys<br>35 | aaa<br>Lys | atg<br>Met | att<br>Ile | aga<br>Arg | cgt<br>Arg<br>40 | ctt<br>Leu | 209 |
| ttt<br>Phe | caa<br>Gln | tat<br>Tyr | acc<br>Thr<br>45 | tca<br>Ser | atg<br>Met | act<br>Thr | ttt<br>Phe | gct<br>Ala<br>50 | tgg<br>Trp | att<br>Ile | ctc<br>Leu | ctc<br>Leu | ttc<br>Phe<br>55 | tta<br>Leu | tcc<br>Ser | 257 |
| gca<br>Ala | gct<br>Ala | tct<br>Ser<br>60 | cca<br>Pro | tca<br>Ser | cta<br>Leu | ggg<br>Gly | gcg<br>Ala<br>65 | ttt<br>Phe | gaa<br>Glu | tgc<br>Cys | ggt<br>Gly | gtg<br>Val<br>70 | cca<br>Pro | cat<br>His | ttt<br>Phe | 305 |
| aaa<br>Lys | ccc<br>Pro | tat<br>Tyr | ata<br>Ile<br>75 | tgg<br>Trp | aaa<br>Lys | tct<br>Ser | ggt<br>Gly | cga<br>Arg<br>80 | att<br>Ile | gtt<br>Val | ggt<br>Gly | gga<br>Gly | act<br>Thr<br>85 | gac<br>Asp | gta<br>Val | 353 |
| cga<br>Arg | cca<br>Pro<br>90 | cac<br>His | tca<br>Ser | cat<br>His | cca<br>Pro<br>95 | tgg<br>Trp | cag<br>Gln | att<br>Ile | caa<br>Gln | ttg<br>Leu<br>100 | tta<br>Leu | aag<br>Lys | tca<br>Ser | gaa<br>Glu | acg<br>Thr | 401 |
| gga<br>Gly<br>105 | ggc<br>Gly | tac<br>Tyr | agc<br>Ser | agc<br>Ser<br>110 | ttg<br>Leu | tgc<br>Cys | ggt<br>Gly | ggt<br>Gly | agt<br>Ser<br>115 | ctt<br>Leu | gtt<br>Val | cat<br>His | ttc<br>Phe | ggt<br>Gly<br>120 | aaa<br>Lys | 449 |
| ccc<br>Pro | tca<br>Ser | aat<br>Asn | ggt<br>Gly | act<br>Thr<br>125 | cga<br>Arg | ttt<br>Phe | gta<br>Val | ctt<br>Leu | acc<br>Thr<br>130 | gcc<br>Ala | gcg<br>Ala | cac<br>His | tgt<br>Cys | ata<br>Ile<br>135 | act<br>Thr | 497 |
| act<br>Thr | agc<br>Ser | aat<br>Asn | atg<br>Met<br>140 | tat<br>Tyr | cca<br>Pro | aga<br>Arg | acg<br>Thr | tca<br>Ser<br>145 | aga<br>Arg | ttt<br>Phe | aca<br>Thr | gtt<br>Val | gtg<br>Val<br>150 | acc<br>Thr | ggt<br>Gly | 545 |
| gcc<br>Ala | cac<br>His | aac<br>Asn<br>155 | atc<br>Ile | aaa<br>Lys | atg<br>Met | cat<br>His | gaa<br>Glu<br>160 | aaa<br>Lys | gaa<br>Glu | aaa<br>Lys | aag<br>Lys | cgc<br>Arg<br>165 | ata<br>Ile | cca<br>Pro | att<br>Ile | 593 |
| act<br>Thr | tcc<br>Ser<br>170 | tat<br>Tyr | tat<br>Tyr | gtt<br>Val | cag<br>Gln | cac<br>His<br>175 | tgg<br>Trp | aac<br>Asn | cct<br>Pro | gtg<br>Val | atg<br>Met<br>180 | aca<br>Thr | aca<br>Thr | aac<br>Asn | gac<br>Asp | 641 |
| att<br>Ile<br>185 | gcg<br>Ala | ttg<br>Leu | ctt<br>Leu | cgc<br>Arg | ctg<br>Leu<br>190 | gca<br>Ala | gaa<br>Glu | act<br>Thr | gtt<br>Val | tat<br>Tyr<br>195 | tat<br>Tyr | aat<br>Asn | gaa<br>Glu | tat<br>Tyr | acc<br>Thr<br>200 | 689 |
| agg<br>Arg | cct<br>Pro | gtc<br>Val | tgt<br>Cys | ttg<br>Leu<br>205 | cca<br>Pro | gaa<br>Glu | cca<br>Pro | aat<br>Asn | gaa<br>Glu<br>210 | gaa<br>Glu | ttg<br>Leu | act<br>Thr | cct<br>Pro | gga<br>Gly<br>215 | gat<br>Asp | 737 |
| att<br>Ile | tgc<br>Cys | gtt<br>Val | gtc<br>Val<br>220 | acc<br>Thr | gga<br>Gly | tgg<br>Trp | ggt<br>Gly | gat<br>Asp<br>225 | acg<br>Thr | act<br>Thr | gaa<br>Glu | aat<br>Asn | gga<br>Gly<br>230 | act<br>Thr | act<br>Thr | 785 |
| tct<br>Ser | aat<br>Asn | act<br>Thr<br>235 | ttg<br>Leu | aag<br>Lys | caa<br>Gln | gtt<br>Val | ggt<br>Gly<br>240 | gtc<br>Val | aaa<br>Lys | att<br>Ile | atg<br>Met | aag<br>Lys<br>245 | aaa<br>Lys | gga<br>Gly | act<br>Thr | 833 |
| tgt<br>Cys | gca<br>Ala<br>250 | aat<br>Asn | gtg<br>Val | aga<br>Arg | agt<br>Ser | gaa<br>Glu<br>255 | gtt<br>Val | att<br>Ile | act<br>Thr | ttt<br>Phe | tgc<br>Cys<br>260 | gct<br>Ala | gga<br>Gly | gct<br>Ala | atg<br>Met | 881 |
| gag<br>Glu<br>265 | ggt<br>Gly | ggt<br>Gly | aaa<br>Lys | gac<br>Asp | agt<br>Ser<br>270 | tgt<br>Cys | caa<br>Gln | ggt<br>Gly | gat<br>Asp | tct<br>Ser<br>275 | ggt<br>Gly | ggc<br>Gly | cca<br>Pro | ctg<br>Leu | ata<br>Ile<br>280 | 929 |
| tgc<br>Cys | aag<br>Lys | aaa<br>Lys | aat<br>Asn | ggg<br>Gly<br>285 | aaa<br>Lys | agt<br>Ser | gtt<br>Val | caa<br>Gln | ttc<br>Phe<br>290 | ggt<br>Gly | gtc<br>Val | gtt<br>Val | agt<br>Ser | tat<br>Tyr<br>295 | ggt<br>Gly | 977 |
| act<br>Thr | gga<br>Gly | tgc<br>Cys | gcc<br>Ala | aga<br>Arg | aaa<br>Lys | ggt<br>Gly | tat<br>Tyr | ccc<br>Pro | gga<br>Gly | gtg<br>Val | tat<br>Tyr | gcc<br>Ala | aaa<br>Lys | gtt<br>Val | cca<br>Pro | 1025 |

-continued

```
Thr Gly Cys Ala Arg Lys Gly Tyr Pro Gly Val Tyr Ala Lys Val Pro
            300                 305                 310 tca tat gtc aca tgg tta aat aaa gct gca aaa gaa ctt gaa aat tct      1073
Ser Tyr Val Thr Trp Leu Asn Lys Ala Ala Lys Glu Leu Glu Asn Ser
            315                 320                 325 cct gaa gga act gta aaa tgg gct tca aaa gaa gat tcg cca gtc gat      1121
Pro Glu Gly Thr Val Lys Trp Ala Ser Lys Glu Asp Ser Pro Val Asp
        330                 335                 340 tta tct act gca tca aga cca act aac cca tat act ggg tca aga ccg      1169
Leu Ser Thr Ala Ser Arg Pro Thr Asn Pro Tyr Thr Gly Ser Arg Pro
345                 350                 355                 360 aca tct cca tct agt gga tca aga ccc aca tat cca tct agt gga tca      1217
Thr Ser Pro Ser Ser Gly Ser Arg Pro Thr Tyr Pro Ser Ser Gly Ser
                365                 370                 375 aga cca aca tct cca tct agt gga tca aga ccc aca tat cca tct agt      1265
Arg Pro Thr Ser Pro Ser Ser Gly Ser Arg Pro Thr Tyr Pro Ser Ser
            380                 385                 390 gga tca aga ccc aca tat cca tct agt gga tca aga cca aca tat cca      1313
Gly Ser Arg Pro Thr Tyr Pro Ser Ser Gly Ser Arg Pro Thr Tyr Pro
        395                 400                 405 tat act gga tca aga cct act cct caa aag cca gta ttt cca tca tac      1361
Tyr Thr Gly Ser Arg Pro Thr Pro Gln Lys Pro Val Phe Pro Ser Tyr
410                 415                 420 caa aaa tat ccg cca gca gtt caa aaa tac att gat agt tta cca agc      1409
Gln Lys Tyr Pro Pro Ala Val Gln Lys Tyr Ile Asp Ser Leu Pro Ser
425                 430                 435                 440 gga acg caa gga acg ctc gaa tac aca gtc aca cag aat gga gtt act      1457
Gly Thr Gln Gly Thr Leu Glu Tyr Thr Val Thr Gln Asn Gly Val Thr
                445                 450                 455 aca aca aca tat tat cac ttt tct aag taa aaatattatg attaattcac       1507
Thr Thr Thr Tyr Tyr His Phe Ser Lys
            460                 465 tactgctctg aacgtaatta aaaaaggaat atttattaag cattttaata tgacacatta    1567
tatatattaa aacagtcaaa tttgaaaaaa aaaaaaaaaa aa                       1609

<210> SEQ ID NO 2
<211> LENGTH: 465
<212> TYPE: PRT
<213> ORGANISM: Trichinella spiralis

<400> SEQUENCE: 2

Met His Lys Ile Thr His Lys Ser Ile Val Ser Arg His Thr Phe Ala
1               5                   10                  15

Val Tyr Leu Leu Val Ser Gly Gln Lys Leu Gln Tyr Ile Tyr Ile Phe
            20                  25                  30

Ile Cys Lys Met Ile Arg Arg Leu Phe Gln Tyr Thr Ser Met Thr Phe
        35                  40                  45

Ala Trp Ile Leu Leu Phe Leu Ser Ala Ala Ser Pro Ser Leu Gly Ala
    50                  55                  60

Phe Glu Cys Gly Val Pro His Phe Lys Pro Tyr Ile Trp Lys Ser Gly
65                  70                  75                  80

Arg Ile Val Gly Gly Thr Asp Val Arg Pro His Ser His Pro Trp Gln
                85                  90                  95

Ile Gln Leu Leu Lys Ser Glu Thr Gly Gly Tyr Ser Ser Leu Cys Gly
            100                 105                 110

Gly Ser Leu Val His Phe Gly Lys Pro Ser Asn Gly Thr Arg Phe Val
        115                 120                 125

Leu Thr Ala Ala His Cys Ile Thr Thr Ser Asn Met Tyr Pro Arg Thr
```

```
                130                 135                 140
Ser Arg Phe Thr Val Val Thr Gly Ala His Asn Ile Lys Met His Glu
145                 150                 155                 160

Lys Glu Lys Lys Arg Ile Pro Ile Thr Ser Tyr Tyr Val Gln His Trp
                165                 170                 175

Asn Pro Val Met Thr Thr Asn Asp Ile Ala Leu Leu Arg Leu Ala Glu
                180                 185                 190

Thr Val Tyr Tyr Asn Glu Tyr Thr Arg Pro Val Cys Leu Pro Glu Pro
                195                 200                 205

Asn Glu Glu Leu Thr Pro Gly Asp Ile Cys Val Thr Gly Trp Gly
210                 215                 220

Asp Thr Thr Glu Asn Gly Thr Thr Ser Asn Thr Leu Lys Gln Val Gly
225                 230                 235                 240

Val Lys Ile Met Lys Lys Gly Thr Cys Ala Asn Val Arg Ser Glu Val
                245                 250                 255

Ile Thr Phe Cys Ala Gly Ala Met Glu Gly Gly Lys Asp Ser Cys Gln
                260                 265                 270

Gly Asp Ser Gly Gly Pro Leu Ile Cys Lys Lys Asn Gly Lys Ser Val
                275                 280                 285

Gln Phe Gly Val Val Ser Tyr Gly Thr Gly Cys Ala Arg Lys Gly Tyr
                290                 295                 300

Pro Gly Val Tyr Ala Lys Val Pro Ser Tyr Val Thr Trp Leu Asn Lys
305                 310                 315                 320

Ala Ala Lys Glu Leu Glu Asn Ser Pro Glu Gly Thr Val Lys Trp Ala
                325                 330                 335

Ser Lys Glu Asp Ser Pro Val Asp Leu Ser Thr Ala Ser Arg Pro Thr
                340                 345                 350

Asn Pro Tyr Thr Gly Ser Arg Pro Thr Ser Pro Ser Ser Gly Ser Arg
                355                 360                 365

Pro Thr Tyr Pro Ser Ser Gly Ser Arg Pro Thr Ser Pro Ser Ser Gly
                370                 375                 380

Ser Arg Pro Thr Tyr Pro Ser Ser Gly Ser Arg Pro Thr Tyr Pro Ser
385                 390                 395                 400

Ser Gly Ser Arg Pro Thr Tyr Pro Tyr Thr Gly Ser Arg Pro Thr Pro
                405                 410                 415

Gln Lys Pro Val Phe Pro Ser Tyr Gln Lys Tyr Pro Pro Ala Val Gln
                420                 425                 430

Lys Tyr Ile Asp Ser Leu Pro Ser Gly Thr Gln Gly Thr Leu Glu Tyr
                435                 440                 445

Thr Val Thr Gln Asn Gly Val Thr Thr Thr Tyr Tyr His Phe Ser
    450                 455                 460

Lys
465

<210> SEQ ID NO 3
<211> LENGTH: 700
<212> TYPE: DNA
<213> ORGANISM: Trichinella spiralis
<220> FEATURE:
<221> NAME/KEY: CDS
<222> LOCATION: (1)..(528)

<400> SEQUENCE: 3 cga gaa aac atg cat tgc caa ttc att ctc tct ttg ctc ctt ttc tct    48
Arg Glu Asn Met His Cys Gln Phe Ile Leu Ser Leu Leu Leu Phe Ser
1               5                   10                  15
```

-continued

| | | |
|---|---|---|
| ttg aac gtc gta ttc ttc gaa gcc gcg aaa tca ctg gat gcc gta gac<br>Leu Asn Val Val Phe Phe Glu Ala Ala Lys Ser Leu Asp Ala Val Asp<br>          20                    25                    30 | 96 |
| gat gaa tta aaa aga tgt act gag aag caa act gaa att tgt gct caa<br>Asp Glu Leu Lys Arg Cys Thr Glu Lys Gln Thr Glu Ile Cys Ala Gln<br> 35                       40                     45 | 144 |
| aca gaa tgc aaa gca gaa gat gca att atg aca gat ctg ctt ctc gag<br>Thr Glu Cys Lys Ala Glu Asp Ala Ile Met Thr Asp Leu Leu Leu Glu<br>50                       55                    60 | 192 |
| gga gaa agc gac att act gat cat cct gac ttc ctt tta tac gca act<br>Gly Glu Ser Asp Ile Thr Asp His Pro Asp Phe Leu Leu Tyr Ala Thr<br>65                       70                   75                   80 | 240 |
| tgc atg caa cgt tgc tgt gca aga ctg aac ggc gct caa gta gct cca<br>Cys Met Gln Arg Cys Cys Ala Arg Leu Asn Gly Ala Gln Val Ala Pro<br>                  85                    90                    95 | 288 |
| ttg aaa gaa gaa gaa aaa cga aga gga cct tca aaa tta ccg ttc caa<br>Leu Lys Glu Glu Glu Lys Arg Arg Gly Pro Ser Lys Leu Pro Phe Gln<br>                       100                105              110 | 336 |
| agc att ttt gaa gtt gct gat caa aaa aca gtt gaa aga tgt gat gaa<br>Ser Ile Phe Glu Val Ala Asp Gln Lys Thr Val Glu Arg Cys Asp Glu<br>          115                    120                  125 | 384 |
| aca atg tgc aag agt tat aga aag aaa tat gaa aat ttg gta gca ttg<br>Thr Met Cys Lys Ser Tyr Arg Lys Lys Tyr Glu Asn Leu Val Ala Leu<br>130                     135                    140 | 432 |
| act tca agc tac aaa aag cta cga tca agc caa gaa ttg aaa gac tac<br>Thr Ser Ser Tyr Lys Lys Leu Arg Ser Ser Gln Glu Leu Lys Asp Tyr<br>145                     150                    155                  160 | 480 |
| aaa caa tgc atc gaa aga tgt gac gca aaa ttg aat gga tta cag taa<br>Lys Gln Cys Ile Glu Arg Cys Asp Ala Lys Leu Asn Gly Leu Gln<br>                       165                    170                  175 | 528 |
| agccagatat gaagaatgga gatatgcatt acaaagaaaa attttaactg aaataatttt | 588 |
| tgttttataa aatctataaa tatcatttct aactgcatta gaattttttt gaagaaaaat | 648 |
| aaaataaaaa aaaaaaaaaa aaaaaaaaaa actcgagggg gggcccggtc cc | 700 |

<210> SEQ ID NO 4
<211> LENGTH: 175
<212> TYPE: PRT
<213> ORGANISM: Trichinella spiralis

<400> SEQUENCE: 4

Arg Glu Asn Met His Cys Gln Phe Ile Leu Ser Leu Leu Leu Phe Ser
1               5                   10                  15

Leu Asn Val Val Phe Phe Glu Ala Ala Lys Ser Leu Asp Ala Val Asp
            20                  25                  30

Asp Glu Leu Lys Arg Cys Thr Glu Lys Gln Thr Glu Ile Cys Ala Gln
        35                  40                  45

Thr Glu Cys Lys Ala Glu Asp Ala Ile Met Thr Asp Leu Leu Leu Glu
    50                  55                  60

Gly Glu Ser Asp Ile Thr Asp His Pro Asp Phe Leu Leu Tyr Ala Thr
65                  70                  75                  80

Cys Met Gln Arg Cys Cys Ala Arg Leu Asn Gly Ala Gln Val Ala Pro
                85                  90                  95

Leu Lys Glu Glu Glu Lys Arg Arg Gly Pro Ser Lys Leu Pro Phe Gln
            100                 105                 110

Ser Ile Phe Glu Val Ala Asp Gln Lys Thr Val Glu Arg Cys Asp Glu
        115                 120                 125

Thr Met Cys Lys Ser Tyr Arg Lys Lys Tyr Glu Asn Leu Val Ala Leu
    130                 135                 140

```
Thr Ser Ser Tyr Lys Lys Leu Arg Ser Ser Gln Glu Leu Lys Asp Tyr
145                 150                 155                 160

Lys Gln Cys Ile Glu Arg Cys Asp Ala Lys Leu Asn Gly Leu Gln
                165                 170                 175
```

<210> SEQ ID NO 5
<211> LENGTH: 10
<212> TYPE: PRT
<213> ORGANISM: Trichinella spiralis

<400> SEQUENCE: 5

```
Pro Ser Ser Gly Ser Arg Pro Thr Tyr Pro
1               5                   10
```

<210> SEQ ID NO 6
<211> LENGTH: 15
<212> TYPE: PRT
<213> ORGANISM: Trichinella spiralis

<400> SEQUENCE: 6

```
Pro Ser Ser Gly Ser Arg Pro Thr Tyr Pro Ser Ser Gly Ser Arg
1               5                   10                  15
```

<210> SEQ ID NO 7
<211> LENGTH: 15
<212> TYPE: PRT
<213> ORGANISM: Trichinella spiralis

<400> SEQUENCE: 7

```
Pro Ser Ser Gly Ser Arg Pro Thr Tyr Pro Tyr Thr Gly Ser Arg
1               5                   10                  15
```

<210> SEQ ID NO 8
<211> LENGTH: 15
<212> TYPE: PRT
<213> ORGANISM: Trichinella spiralis

<400> SEQUENCE: 8

```
Arg Pro Thr Ser Pro Ser Ser Gly Ser Arg Pro Thr Tyr Pro Ser
1               5                   10                  15
```

<210> SEQ ID NO 9
<211> LENGTH: 46
<212> TYPE: PRT
<213> ORGANISM: Trichinella spiralis

<400> SEQUENCE: 9

```
Pro Ser Ser Gly Ser Arg Pro Thr Tyr Pro Ser Ser Gly Ser Arg Pro
1               5                   10                  15

Thr Ser Pro Ser Ser Gly Ser Arg Pro Thr Tyr Pro Ser Ser Gly Ser
                20                  25                  30

Arg Pro Thr Tyr Pro Ser Ser Gly Ser Arg Pro Thr Tyr Pro
                35                  40                  45
```

<210> SEQ ID NO 10
<211> LENGTH: 67
<212> TYPE: PRT
<213> ORGANISM: Trichinella spiralis

<400> SEQUENCE: 10

```
Ser Arg Pro Thr Asn Pro Tyr Thr Gly Ser Arg Pro Thr Ser Pro Ser
1               5                   10                  15

Ser Gly Ser Arg Pro Thr Tyr Pro Ser Ser Gly Ser Arg Pro Thr Ser
```

```
                    20                  25                  30

Pro Ser Ser Gly Ser Arg Pro Thr Tyr Pro Ser Ser Gly Ser Arg Pro
            35                  40                  45

Thr Tyr Pro Ser Ser Gly Ser Arg Pro Thr Tyr Pro Tyr Thr Gly Ser
        50                  55                  60

Arg Pro Thr
65

<210> SEQ ID NO 11
<211> LENGTH: 134
<212> TYPE: PRT
<213> ORGANISM: Trichinella spiralis

<400> SEQUENCE: 11

Glu Asn Ser Pro Glu Gly Thr Val Lys Trp Ala Ser Lys Glu Asp Ser
1               5                   10                  15

Pro Val Asp Leu Ser Thr Ala Ser Arg Pro Thr Asn Pro Tyr Thr Gly
            20                  25                  30

Ser Arg Pro Thr Ser Pro Ser Gly Ser Arg Pro Thr Tyr Pro Ser
        35                  40                  45

Ser Gly Ser Arg Pro Thr Ser Pro Ser Gly Ser Arg Pro Thr Tyr
    50                  55                  60

Pro Ser Ser Gly Ser Arg Pro Thr Tyr Pro Ser Ser Gly Ser Arg Pro
65                  70                  75                  80

Thr Tyr Pro Tyr Thr Gly Ser Arg Pro Thr Pro Gln Lys Pro Val Phe
                85                  90                  95

Pro Ser Tyr Gln Lys Tyr Pro Pro Ala Val Gln Lys Tyr Ile Asp Ser
            100                 105                 110

Leu Pro Ser Gly Thr Gln Gly Thr Leu Glu Tyr Thr Val Thr Gln Asn
        115                 120                 125

Gly Val Thr Thr Thr Thr
    130

<210> SEQ ID NO 12
<211> LENGTH: 22
<212> TYPE: DNA
<213> ORGANISM: Artificial Sequence
<220> FEATURE:
<223> OTHER INFORMATION: NBL1CtermF

<400> SEQUENCE: 12
caccgaaaat tctcctgaag ga                                         22

<210> SEQ ID NO 13
<211> LENGTH: 18
<212> TYPE: DNA
<213> ORGANISM: Artificial Sequence
<220> FEATURE:
<223> OTHER INFORMATION: NBL1CtermR

<400> SEQUENCE: 13
tgttgttgta gtaactcc                                              18

<210> SEQ ID NO 14
<211> LENGTH: 15
<212> TYPE: PRT
<213> ORGANISM: Trichinella spiralis

<400> SEQUENCE: 14

Asn Ser Pro Glu Gly Thr Val Lys Trp Ala Ser Lys Glu Asp Ser
1               5                   10                  15
```

<210> SEQ ID NO 15
<211> LENGTH: 15
<212> TYPE: PRT
<213> ORGANISM: Trichinella spiralis

<400> SEQUENCE: 15

Ala Ser Lys Glu Asp Ser Pro Val Asp Leu Ser Thr Ala Ser Arg
1               5                   10                  15

<210> SEQ ID NO 16
<211> LENGTH: 15
<212> TYPE: PRT
<213> ORGANISM: Trichinella spiralis

<400> SEQUENCE: 16

Leu Ser Thr Ala Ser Arg Pro Thr Asn Pro Tyr Thr Gly Ser Arg
1               5                   10                  15

<210> SEQ ID NO 17
<211> LENGTH: 15
<212> TYPE: PRT
<213> ORGANISM: Trichinella spiralis

<400> SEQUENCE: 17

Pro Tyr Thr Gly Ser Arg Pro Thr Ser Pro Ser Ser Gly Ser Arg
1               5                   10                  15

<210> SEQ ID NO 18
<211> LENGTH: 15
<212> TYPE: PRT
<213> ORGANISM: Trichinella spiralis

<400> SEQUENCE: 18

Pro Ser Ser Gly Ser Arg Pro Thr Ser Pro Ser Ser Gly Ser Arg
1               5                   10                  15

<210> SEQ ID NO 19
<211> LENGTH: 15
<212> TYPE: PRT
<213> ORGANISM: Trichinella spiralis

<400> SEQUENCE: 19

Pro Tyr Thr Gly Ser Arg Pro Thr Pro Gln Lys Pro Val Phe Pro
1               5                   10                  15

<210> SEQ ID NO 20
<211> LENGTH: 15
<212> TYPE: PRT
<213> ORGANISM: Trichinella spiralis

<400> SEQUENCE: 20

Gln Lys Pro Val Phe Pro Ser Tyr Gln Lys Tyr Pro Pro Ala Val
1               5                   10                  15

<210> SEQ ID NO 21
<211> LENGTH: 15
<212> TYPE: PRT
<213> ORGANISM: Trichinella spiralis

<400> SEQUENCE: 21

Lys Tyr Pro Pro Ala Val Gln Lys Tyr Ile Asp Ser Leu Pro Ser
1               5                   10                  15

<210> SEQ ID NO 22

```
<211> LENGTH: 19
<212> TYPE: DNA
<213> ORGANISM: Artificial Sequence
<220> FEATURE:
<223> OTHER INFORMATION: 411 forward primer

<400> SEQUENCE: 22
cacccgagaa aacatgcat                                                     19

<210> SEQ ID NO 23
<211> LENGTH: 20
<212> TYPE: DNA
<213> ORGANISM: Artificial Sequence
<220> FEATURE:
<223> OTHER INFORMATION: 411 reverse primer

<400> SEQUENCE: 23
tccattcaat tttgcgtcac                                                    20

<210> SEQ ID NO 24
<211> LENGTH: 291
<212> TYPE: PRT
<213> ORGANISM: Artificial Sequence
<220> FEATURE:
<223> OTHER INFORMATION: THX-NBL1(Cterm) protein

<400> SEQUENCE: 24

Met Gly Ser Asp Lys Ile Ile His Leu Thr Asp Asp Ser Phe Asp Thr
1               5                   10                  15

Asp Val Leu Lys Ala Asp Gly Ala Ile Leu Val Asp Phe Trp Ala His
            20                  25                  30

Trp Cys Gly Pro Cys Lys Met Ile Ala Pro Ile Leu Asp Glu Ile Ala
        35                  40                  45

Asp Glu Tyr Gln Gly Lys Leu Thr Val Ala Lys Leu Asn Ile Asp His
    50                  55                  60

Asn Pro Gly Thr Ala Pro Lys Tyr Gly Ile Arg Gly Ile Pro Thr Leu
65                  70                  75                  80

Leu Leu Phe Lys Asn Gly Glu Val Ala Ala Thr Lys Val Gly Ala Leu
                85                  90                  95

Ser Lys Gly Gln Leu Lys Glu Phe Leu Asp Ala Asn Leu Ala Gly Ser
            100                 105                 110

Gly Ser Gly Asp Asp Asp Asp Lys Leu Gly Ile Asp Pro Phe Thr Glu
        115                 120                 125

Asn Ser Pro Glu Gly Thr Val Lys Trp Ala Ser Lys Glu Asp Ser Pro
    130                 135                 140

Val Asp Leu Ser Thr Ala Ser Arg Pro Thr Asn Pro Tyr Thr Gly Ser
145                 150                 155                 160

Arg Pro Thr Ser Pro Ser Gly Ser Arg Pro Thr Tyr Pro Ser Ser
                165                 170                 175

Gly Ser Arg Pro Thr Ser Pro Ser Ser Gly Ser Arg Pro Thr Tyr Pro
            180                 185                 190

Ser Ser Gly Ser Arg Pro Thr Tyr Pro Ser Ser Gly Ser Arg Pro Thr
        195                 200                 205

Tyr Pro Tyr Thr Gly Ser Arg Pro Thr Pro Gln Lys Pro Val Phe Pro
    210                 215                 220

Ser Tyr Gln Lys Tyr Pro Ala Val Gln Lys Tyr Ile Asp Ser Leu
225                 230                 235                 240

Pro Ser Gly Thr Gln Gly Thr Leu Glu Tyr Thr Val Thr Gln Asn Gly
                245                 250                 255
```

```
Val Thr Thr Thr Thr Lys Gly Glu Leu Lys Leu Glu Gly Lys Pro Ile
            260                 265                 270

Pro Asn Pro Leu Leu Gly Leu Asp Ser Thr Arg Thr Gly His His His
        275                 280                 285

His His His
    290

<210> SEQ ID NO 25
<211> LENGTH: 330
<212> TYPE: PRT
<213> ORGANISM: Artificial Sequence
<220> FEATURE:
<223> OTHER INFORMATION: THX-411 protein

<400> SEQUENCE: 25

Met Gly Ser Asp Lys Ile Ile His Leu Thr Asp Asp Ser Phe Asp Thr
1               5                   10                  15

Asp Val Leu Lys Ala Asp Gly Ala Ile Leu Val Asp Phe Trp Ala His
            20                  25                  30

Trp Cys Gly Pro Cys Lys Met Ile Ala Pro Ile Leu Asp Glu Ile Ala
        35                  40                  45

Asp Glu Tyr Gln Gly Lys Leu Thr Val Ala Lys Leu Asn Ile Asp His
    50                  55                  60

Asn Pro Gly Thr Ala Pro Lys Tyr Gly Ile Arg Gly Ile Pro Thr Leu
65                  70                  75                  80

Leu Leu Phe Lys Asn Gly Glu Val Ala Ala Thr Lys Val Gly Ala Leu
                85                  90                  95

Ser Lys Gly Gln Leu Lys Glu Phe Leu Asp Ala Asn Leu Ala Gly Ser
            100                 105                 110

Gly Ser Gly Asp Asp Asp Asp Lys Leu Gly Ile Asp Pro Phe Thr Arg
        115                 120                 125

Glu Asn Met His Cys Gln Phe Ile Leu Ser Leu Leu Leu Phe Ser Leu
    130                 135                 140

Asn Val Val Phe Phe Glu Ala Ala Lys Ser Leu Asp Ala Val Asp Asp
145                 150                 155                 160

Glu Leu Lys Arg Cys Thr Glu Lys Gln Thr Glu Ile Cys Ala Gln Thr
                165                 170                 175

Glu Cys Lys Ala Glu Asp Ala Ile Met Thr Asp Leu Leu Leu Glu Gly
            180                 185                 190

Glu Ser Asp Ile Thr Asp His Pro Asp Phe Leu Leu Tyr Ala Thr Cys
        195                 200                 205

Met Gln Arg Cys Cys Ala Arg Leu Asn Gly Ala Gln Val Ala Pro Leu
    210                 215                 220

Lys Glu Glu Glu Lys Arg Arg Gly Pro Ser Lys Leu Pro Phe Gln Ser
225                 230                 235                 240

Ile Phe Glu Val Ala Asp Gln Lys Thr Val Glu Arg Cys Asp Glu Thr
                245                 250                 255

Met Cys Lys Ser Tyr Arg Lys Lys Tyr Glu Asn Leu Val Ala Leu Thr
            260                 265                 270

Ser Ser Tyr Lys Lys Leu Arg Ser Ser Gln Glu Leu Lys Asp Tyr Lys
        275                 280                 285

Gln Cys Ile Glu Arg Cys Asp Ala Lys Leu Asn Gly Lys Gly Glu Leu
    290                 295                 300
```

```
Lys Leu Glu Gly Lys Pro Ile Pro Asn Pro Leu Leu Gly Leu Asp Ser
305                 310                 315                 320

Thr Arg Thr Gly His His His His His
                325             330
```